United States Patent [19]
Yamada et al.

[11] Patent Number: 5,807,883
[45] Date of Patent: Sep. 15, 1998

[54] 2-OXOINDOLINE DERIVATIVE

[75] Inventors: Koichiro Yamada, Minamisaitama-gun; Masataka Hikota, Shiki; Toshiro Shikano, Kawaguchi; Masaaki Nagasaki, Omiya, all of Japan

[73] Assignee: Tanabe Seiyaku Co., Ltd., Osaka, Japan

[21] Appl. No.: 648,191

[22] PCT Filed: Nov. 25, 1994

[86] PCT No.: PCT/JP94/01990

§ 371 Date: May 24, 1996

§ 102(e) Date: May 24, 1996

[87] PCT Pub. No.: WO95/14668

PCT Pub. Date: Jun. 1, 1995

[30] Foreign Application Priority Data

Nov. 26, 1993 [JP] Japan .................................. 5-296183

[51] Int. Cl.$^6$ ................ A61K 31/40; A61K 31/415; A61K 31/44; A61K 31/47; C07D 209/02; C07D 235/04; C07D 217/00; C07D 451/00

[52] U.S. Cl. ................ 514/418; 514/235.2; 514/249; 514/294; 514/307; 514/314; 514/339; 514/381; 514/394; 514/411; 514/414; 544/144; 544/355; 546/94; 546/145; 546/146; 546/147; 546/169; 546/277.7; 548/253; 548/305.1; 548/428; 548/454; 548/455; 548/463; 548/465; 548/467; 548/483

[58] Field of Search .................................. 548/483, 455, 548/465, 253, 454, 467, 305.1, 463, 428; 514/418, 294, 414, 307, 314, 339, 235.2, 381, 249, 394, 411; 546/146, 147, 169, 277.7, 94; 544/144, 355

[56] References Cited

U.S. PATENT DOCUMENTS 4,985,448  1/1991  Zilch et al. .............................. 514/339

FOREIGN PATENT DOCUMENTS

| | | |
|---|---|---|
| 0304223 | 2/1989 | European Pat. Off. . |
| 0348523 | 1/1990 | European Pat. Off. . |
| 0360079 | 3/1990 | European Pat. Off. . |
| 6468369 | 3/1989 | Japan . |
| 228181 | 1/1990 | Japan . |
| 2111774 | 4/1990 | Japan . |
| 9419322 | 9/1994 | WIPO . |

OTHER PUBLICATIONS

Talley, N.J. *Alimentary Pharmacology and Therapeutics*, vol. 9, pp. 107–115 (1995).

Esaki, T. et al. *Chemical Abstract*, No. 122:55893, Obtained via STN Databases (1995).

Emura, T. et al. *Derwent World Patent Index*, No. 94–294220 (1994).

Zydowsky, T.M. et al. *J. Org. Chem.*, vol. 53, pp. 5607–5616 (1988).

Niederau, C. et al. *Hepato–Gastroenterology*, vol. 40, p. 538 (1993 Dec.), Abstract Only Obtained via Medline.

Greenberger, N.J. et al. *Harrison's Principles of Internal Medicine*, vol. 2 (McGraw–Hill, New York), ed. by Isselbacher, K.J. et al., pp. 1520–1532 (1994).

Rothstein, R.D. et al. *Internal Medicine* (Mosby, St. Louis), ed. by Stein, J.H. et al., pp. 436–445 (1994).

Schulze–Delrieu, K.S. et al. *Internal Medicine* (Mosby, St. Louis), ed. by Stein, J.H. et al., pp. 390–395 (1994).

*Primary Examiner*—Mukund J. Shah
*Assistant Examiner*—Brenda Coleman
*Attorney, Agent, or Firm*—Birch, Stewart, Kolasch & Birch, LLP

[57] ABSTRACT

Disclosed is a 2-oxoindoline derivative represented by the formula (I):

wherein Ring A represents a benzene ring which is substituted in the 5-position or 6-position by a lower alkyl group or lower alkoxy group, $R^1$ represents a phenyl group which is substituted by a halogen atom, a lower alkyl group or a lower alkoxy group, $R^2$ represents a naphthyl group, indolyl group, isoquinolyl group, benzimidazolyl group or a group represented by the formula:

wherein n represents 1 or 2, $R^3$ represents a lower alkyl group which is substituted by a carboxyl group, a cyano group or a tetrazolyl group, O represents a single bonding arm, and Y represents a single bonding arm, or a pharmaceutically acceptable salt thereof.

11 Claims, No Drawings

2-OXOINDOLINE DERIVATIVE

This application is a 371 of PCT/JP94/01990 filed Nov. 25, 1994.

TECHNICAL FIELD

This invention relates to a novel 2-oxoindoline derivative having an excellent antagonistic action on cholecystokinin and useful for preventing and treating pancreatic disorder and gastrointestinal diseases, etc. and a process for preparing the same.

BACKGROUND ART

Cholecystokinin (CCK) is a brain-gut peptide existing in a gastrointestinal tissue and a central nervous system, has been known as a substance which is concerned with control of pancreatic exocrine secretion and control of appetite, and has been considered to have actions of promoting motility of colon, contracting gallbladder, promoting secretion of pancreatic enzymes, controlling emptying of gastric content, etc. Further, cholecystokinin coexists with dopamine in a central nervous system so that it has been considered to have a role concerned with mechanism of a dopaminergic system.

It has been considered that a substance having an antagonistic action on this cholecystokinin is effective for preventing or treating pancreatic disorder and gastrointestinal diseases, etc. so that a number of antagonists have been studied up to the present. For example, as a cholecystokinin antagonist, there have been known amino acid derivatives such as benzotript, etc. However, such derivatives are not necessarily satisfactory in that activities thereof are relatively weak, duration of action is short, and they are unstable and poor in absorption, etc.

As a non-peptide type antagonist, there have been disclosed a benzodiazepine compound in Japanese Provisional Patent Publication No. 111774/1990 and a thienoazepine compound in Japanese Provisional Patent Publication No. 28181/1990. Further, in Japanese Provisional Patent Publication No. 68369/1989, there have been disclosed β-carboline derivatives including a compound of the formula (V):

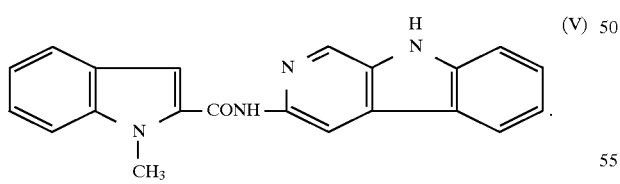

An object of the present invention is to provide a novel 2-oxoindoline derivative having a further excellent antagonistic action on cholecystokinin and useful as a medicine and a pharmaceutically acceptable salt thereof, and a process for preparing the same.

DISCLOSURE OF THE INVENTION

The present invention is a 2-oxoindoline derivative represented by the formula (I):

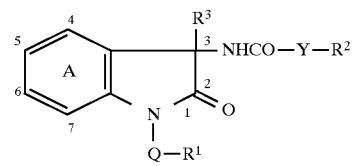

(wherein Ring A represents a substituted or unsubstituted benzene ring, $R^1$ represents hydrogen atom, a cycloalkyl group, a substituted or unsubstituted aryl group, a nitrogen-containing heterocyclic group, an oxygen-containing heterocyclic group, a sulfur-containing heterocyclic group, a heterocyclic group containing nitrogen atom and oxygen atom, a heterocyclic group containing nitrogen atom and sulfur atom, a lower alkoxy group, a carboxyl group which may be esterified, cyano group, a lower alkylthio group, a lower alkylsulfinyl group, a lower alkylsulfonyl group, an oxiranyl group or a 2-(lower alkylthio)-1-hydroxyethyl group, $R^2$ represents a substituted or unsubstituted aryl group, a group represented by the formula:

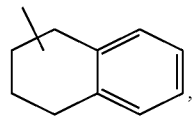

a substituted or unsubstituted nitrogen-containing heteromonocyclic group, a substituted or unsubstituted nitrogen-containing heterobicyclic group, a group represented by the formula:

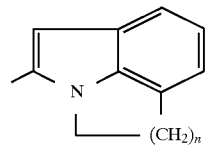

(wherein n represents 1 or 2.),
an oxygen-containing heterocyclic group, a sulfur-containing heterocyclic group, a heterocyclic group containing nitrogen atom and oxygen atom or a heterocyclic group containing nitrogen atom and sulfur atom, $R^3$ represents a substituted or unsubstituted lower alkyl group, Q represents a single bonding arm or a lower alkylene group, Y represents a single bonding arm, a lower alkylene group or a lower alkenylene group.),
and a pharmaceutically acceptable salt thereof, and a process for preparing the same.

Best Mode for Practicing the Invention

The desired compound (I) of the present invention is a medical compound having an excellent antagonistic action on cholecystokinin and useful as a prophylactic or treating agent of pancreatic disorder and gastrointestinal diseases.

As a specific example of the desired compound of the present invention, there may be mentioned a compound of the formula (I) wherein Ring A is a benzene ring which may be substituted by a group selected from a lower alkyl group and a lower alkoxy group; $R^1$ is hydrogen atom; a cycloalkyl group; an aryl group which may be substituted by a group selected from a halogen atom, a lower alkyl group, hydroxy group and a lower alkoxy group; a nitrogen-containing heterocyclic group; an oxygen-containing heterocyclic group; a sulfur-containing heterocyclic group; a heterocyclic group containing nitrogen atom and oxygen atom; a heterocyclic group containing nitrogen atom and sulfur atom; a lower alkoxy group; a carboxyl group which may be esterified; cyano group; a lower alkylthio group; a lower alkylsulfinyl group; a lower alkylsulfonyl group; an oxiranyl group; or a 2-(lower alkylthio)-1-hydroxyethyl group; $R^2$ is an aryl group which may be substituted by a group selected from a halogen atom, hydroxy group and a lower alkoxy group; a group represented by the formula:

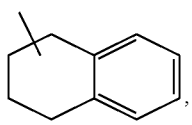

a nitrogen-containing heteromonocyclic group or a nitrogen-containing heterobicyclic group each of which may be substituted by a group selected from a formyl group, a lower alkoxycarbonyl group and a cyano-lower alkyl group; a group represented by the formula:

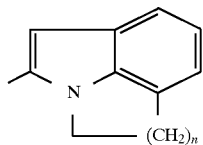

(wherein n represents 1 or 2.);

an oxygen-containing heterocyclic group; a sulfur-containing heterocyclic group; a heterocyclic group containing nitrogen atom and oxygen atom; or a heterocyclic group containing nitrogen atom and sulfur atom; and $R^3$ is a lower alkyl group which may be substituted by a group selected from a carboxyl group which may be esterified, cyano group and tetrazolyl group.

As the aryl group, there may be mentioned phenyl group or naphthyl group. As the nitrogen-containing heteromonocyclic group, there may be mentioned pyridyl group, pyrrolyl group, imidazolyl group, pyrazolyl group, pyrazinyl group, pyrimidyl group or pyridazinyl group. As the nitrogen-containing heterobicyclic group, there may be mentioned indolyl group, quinolyl group, isoquinolyl group, tetrahydroisoquinolyl group, benzimidazolyl group and quinoxalinyl group. As the nitrogen-containing heterocyclic group, there may be mentioned pyrrolyl group, pyridyl group, imidazolyl group, pyrazolyl group, pyrazinyl group, pyrimidyl group, pyridazinyl group, indolyl group, quinolyl group, isoquinolyl group, tetrahydroisoquinolyl group, benzimidazolyl group, quinoxalinyl group, carbazolyl group, carbolinyl group or a group represented by the formula:

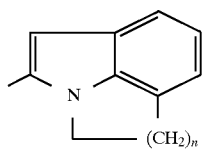

(wherein n represents 1 or 2.).

As the oxygen-containing heterocyclic group, there may be mentioned furyl group, benzofuranyl group, coumaryl group, chromenyl group or chromanyl group. As the sulfur-containing heterocyclic group, there may be mentioned thienyl group, benzothiophenyl group or thianthrenyl group. As the heterocyclic group containing nitrogen atom and oxygen atom, there may be mentioned morpholinyl group, oxazolyl group, isoxazolyl group, benzoxazolyl group or isobenzoxazolyl group. As the heterocyclic group containing nitrogen atom and sulfur atom, there may be mentioned thiazolyl group, isothiazolyl group, benzothiazolyl group or isobenzothiazolyl group.

Among the desired compounds of the present invention, as a preferred compound in view of pharmaceutical effects, there may be mentioned a compound of the formula (I) wherein Ring A is a benzene ring which is substituted by a group selected from a lower alkyl group and a lower alkoxy group; $R^1$ is hydrogen atom; a cycloalkyl group; or a phenyl group which is substituted by a group selected from a halogen atom, a lower alkyl group and a lower alkoxy group; $R^2$ is a phenyl group which is substituted by a group selected from a halogen atom and a lower alkoxy group; naphthyl group;, indolyl group; isoquinolyl group; benzimidazolyl group; or a group represented by the formula:

(wherein n represents 1 or 2.);

$R^3$ is a lower alkyl group which may be substituted by a group selected from carboxyl group, cyano group and a tetrazolyl group; and Y is a single bonding arm or a lower alkenylene group.

As a more preferred compound in view of pharmaceutical effects, there may be mentioned a compound of the formula (I) wherein Ring A is a benzene ring which is substituted at the 5-position or 6-position by a group selected from a lower alkyl group and a lower alkoxy group, $R^1$ is a phenyl group which is substituted by a group selected from a halogen atom, a lower alkyl group and a lower alkoxy group, $R^2$ is naphthyl group, indolyl group, isoquinolyl group, benzimidazolyl group or a group represented by the formula:

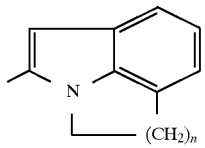

(wherein n represents 1 or 2.), $R^3$ is a lower alkyl group which is substituted by a group selected from carboxyl group and tetrazolyl group, Q is a single bonding arm, and Y is a single bonding arm.

As the most preferred compound in view of pharmaceutical effects, there may be mentioned a compound of the formula (I) wherein Ring A is a benzene ring substituted in the 6-position by a group selected from a lower alkyl group and a lower alkoxy group, $R^1$ is a halogenophenyl group, $R^2$ is isoquinolyl group, and $R^3$ is a carboxyl-lower alkyl group.

In the desired compound (I), optical isomers based on asymmetric carbon atom may exist. Both of these optical isomers and a mixture thereof are included in the present invention.

The desired compound of the present invention can be used for medical uses in the free form or in the form of a pharmaceutically acceptable salt. As the pharmaceutically acceptable salt, there may be mentioned an acid addition salt with an inorganic acid or an organic acid, and a salt with an inorganic base, an organic base or an amino acid, for example, hydrochloride, sulfate, hydrobromide, methanesulfonate, fumarate, maleate, an alkali metal (sodium, potassium, etc.) salt, a methylamine salt, a diethylamine salt, a triethylamine salt, a salt with lysine, etc.

Among the desired compounds (I) of the present invention, when $R^1$ is an esterified carboxyl group and/or $R^3$ is an esterified carboxyl group-substituted lower alkyl group, as an example of an ester residue, there may be mentioned a lower alkyl group, a halogen-substituted lower alkyl group, a phenyl-lower alkyl group, a phenacyl group, etc. Particularly, a lower alkyl group is preferred.

The desired compound (I) and a pharmaceutically acceptable salt thereof can be administered orally and parenterally, and can be generally administered to mammals including a human being in the form of a generally used medical composition such as a capsule, a microcapsule, a tablet, a granule, a powder, a troche, a syrup, an aerosol, an inhalation, a solution, an injection, a suspension, an emulsion, a suppository, etc.

The medical composition according to the present invention may contain various organic or inorganic carrier substances generally used for medicines, such as an excipient, for example, sucrose, starch, mannitol, sorbitol, lactose, glucose, cellulose, talc, calcium phosphate, calcium carbonate, etc.; a binder, for example, cellulose, methyl cellulose, hydroxypropyl cellulose, polypropyl pyrrolidone, gelatin, gum arabic, polyethylene glycol, sucrose, starch, etc.; a disintegrating agent, for example, starch, carboxymethyl cellulose, a calcium salt of carboxymethyl cellulose, hydroxypropyl starch, sodium glycol starch, sodium hydrogen carbonate, calcium phosphate, calcium citrate, etc.; a lubricant, for example, magnesium stearate, talc, sodium lauryl sulfate, etc.; a fragrant, for example, citric acid, menthol, glycine, orange powder, etc.; a preservative, for example, sodium benzoate, sodium hydrogen sulfite, methylparaben, propylparaben, etc.; a stabilizer, for example, citric acid, sodium citrate, acetic acid, etc.; a suspending agent, for example, methyl cellulose, polyvinyl pyrrolidone, aluminum stearate, etc.; a dispersant; an aqueous diluent, for example, water; and a base wax, for example, cacao butter, polyethylene glycol, illuminating kerosine, etc.

The dose of the desired compound (I) of the present invention or a pharmaceutically acceptable salt thereof varies depending on age, body weight and state of a patient or an administration method, but it is generally 0.01 mg/kg to 50 mg/kg per day.

According to the present invention, the 2-oxoindoline derivative (I) which is a desired compound can be prepared by Method (A): reacting an amine compound represented by the formula (II):

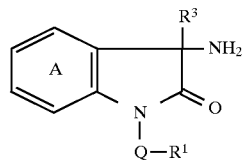
(II)

(wherein Ring A, $R^1$, $R^3$ and Q have the same meanings as described above.), or a salt thereof with a carboxylic acid compound represented by the formula (III):

$HO_2C—Y—R^2$     (III)

(wherein $R^2$ and Y have the same meanings as described above.), a reactive derivative thereof or a salt thereof, or Method (B): reacting a compound represented by the formula (IV):

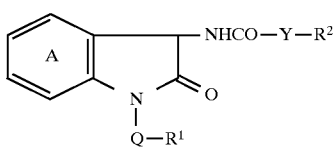
(IV)

(wherein Ring A, $R^1$, $R^2$, Q and Y have the same meanings as described above.), or a salt thereof with an alkylating agent corresponding to $R^3$.

The reactive derivative of the compound (III) may include acid halides, active esters and acid anhydrides, preferably acid halides such as acid chloride, etc.

As the alkylating agent corresponding to $R^3$ to be used in the reaction with the compound (IV), there may be mentioned, for example, an alkyl halide compound represented by $R^3—X^1$ (where $X^1$ represents a halogen atom and $R^3$ has the same meaning as described above.), an alkene compound represented by $CH_2=CH—R^{31}$ (where $R^{31}$ is a substituted or unsubstituted lower alkyl group having carbon atoms which are minus 2 from the carbon atoms possessed by $R^3$), etc.

As the salts of the compounds (II) and (IV), there may be used, for example, a salt with an inorganic acid such as hydrochloric acid, sulfuric acid, etc. As the salt of the compound (III), there may be used, for example, a salt with an inorganic base such as an alkali metal salt, etc. in addition to the above salt with an inorganic acid.

Method (A)

The reaction of the amine compound (II) or a salt thereof and the carboxylic acid compound (III), a reactive derivative thereof or a salt thereof can be carried out easily according to the conventional method. For example, the reaction of the amine compound (II) or a salt thereof and an reactive derivative of the carboxylic acid compound (III) or a salt thereof is carried out in a solvent, if necessary, in the presence of an acid acceptor, at a temperature of under cooling to a boiling point of a solvent used.

The solvent to be used is not particularly limited so long as it is a solvent inactive to the reaction, and may include, for example, water, alcohols such as methanol, ethanol, propanol, butanol, etc.; ethers such as tetrahydrofuran, diethyl ether, dioxane, etc.; esters such as methyl acetate, ethyl acetate, etc.; hydrocarbons such as petroleum ether, hexane, cyclohexane, etc.; halogenated hydrocarbons such as dichloromethane, dichloroethane, chloroform, etc.; aromatic hydrocarbons such as benzene, toluene, xylene, etc.; amides such as N,N-dimethylformamide, N,N-dimethylacetamide, etc., dimethyl sulfoxide and a mixed solvent thereof, etc.

As the acid acceptor to be used depending on necessity, there may be mentioned an organic base such as triethylamine, pyridine, picoline, N-methylmorpholine, etc.; an alkali metal hydroxide such as sodium hydroxide, potassium hydroxide, etc.; an alkali metal carbonate such as sodium carbonate, sodium hydrogen carbonate, potassium carbonate, etc. and others, preferably triethylamine, pyridine, etc. In case of a mixed solvent with water, sodium hydrogen carbonate, potassium carbonate, etc. are preferred.

Further, the reaction of the amine compound (II) or a salt thereof and the free carboxylic acid compound (III) or a salt thereof can be carried out in a solvent in the presence of a dehydrating agent.

The dehydrating agent is preferably one used for amide synthesis and may include, for example, dicyclohexyl carbodiimide, N-ethyl-N'-diethylaminopropylcarbodiimide hydrochloride, N-methyl-2-chloropyridinium iodide, 1-(3- dimethylaminopropyl)-3-ethylcarbodiimide hydrochloride, a BOP reagent [benzotriazol-1-yloxytris-(dimethylamino) phosphonium hexafluorophosphate], diphenylphosphoric acid azide (DPPA), etc. If desired, an active ester reagent such as 1-hydroxybenzotriazole, etc. may be used in combination with the dehydrating agent.

As the solvent, there may be suitably used those described above. The reaction proceeds suitably under cooling to under heating.

The present reaction proceeds without racemization so that when an optically active starting material is used, an optically active desired compound can be obtained.

Method (B)

The reaction of the compound (IV) or a salt thereof and the alkylating agent corresponding to $R^3$ can be carried out according to the conventional method. For example, the reaction of the compound (IV) or a salt thereof and the alkyl halide compound or the alkene compound proceeds suitably in a solvent in the presence of a base. As the base, there may be mentioned an alkali metal carbonate such as sodium carbonate, potassium carbonate, sodium hydrogen carbonate, potassium hydrogen carbonate, etc., an alkali metal hydroxide such as sodium hydroxide, potassium hydroxide, etc., or an organic base such as 1,8-diazabicyclo-[5.4.0]-undec-7-ene, etc. As the solvent, there may be used amides such as N,N-dimethylformamide, N,N-dimethylacetamide, etc., ketones such as acetone, methyl ethyl ketone, etc., halogenated hydrocarbons such as dichloromethane, dichloroethane, etc. and also dimethyl sulfoxide, ethyl acetate, tetrahydrofuran, dioxane, toluene and a mixed solvent thereof, etc. The reaction proceeds suitably under cooling to under heating, for example, at a temperature of 0° C. to 100° C.

The desired compound (I) of the present invention can be also prepared by mutually converting the desired compound obtained as described above into another desired compound according to the conventional method. Such a mutually converting reaction between the desired compounds may be selected suitably depending on the kind of a functional group possessed by the compounds and may be carried out by, for example, the following (a) or (b).

Method (a)

The desired compound (I) in which Q is a lower alkylene group can be prepared by reacting the desired compound (I) in which Q is a single bonding arm and $R^1$ is hydrogen atom with an alkylating agent corresponding to a group: —$Q^1$—$R^1$ (where $Q^1$ represents a lower alkylene group, and $R^1$ has the same meaning as described above.). This reaction can be carried out in the same manner as in Method (B) described above.

Method (b)

The desired compound (I) in which $R^1$ is carboxyl group and/or $R^3$ is a carboxyl-lower alkyl group can be prepared by removing an ester residue of the corresponding desired compound (I) in which carboxyl group is esterified. Removal of the ester residue can be carried out by hydrolyzing the desired compound (I) in which carboxyl group is esterified, by treating it with an acid or an alkaline reagent in a solvent. As the acid, there may be mentioned a mineral acid such as hydrochloric acid, hydrobromic acid, sulfuric acid, etc. and an inorganic or organic acid such as trifluoroacetic acid, benzenesulfonic acid, p-toluene-sulfonic acid, etc. As the alkaline reagent, there may be mentioned an inorganic base such as an alkali metal hydroxide (e.g. sodium hydroxide and potassium hydroxide), etc.

As the solvent, there may be mentioned, for example, water, methanol, ethanol, isopropanol, acetone, acetonitrile, hexane, cyclohexane, benzene, toluene, chloroform, dichloromethane, dichloroethane, dioxane, tetrahydrofuran, N,N-dimethylformamide, N,N-dimethylacetamide, dimethyl sulfoxide or a mixed solvent thereof, etc. The reaction proceeds suitably at a temperature of under cooling to a boiling point of a solvent used.

Further, the desired compounds (I) of the present invention can be mutually converted according to the conventional method as described below.

For example, the desired compound (I) in which $R^1$ is a lower alkylthio group can be converted into a corresponding sulfinyl compound or sulfonyl compound by oxidation. Further, the desired compound (I) in which $R^1$ is oxiranyl group can be converted into a desired compound in which $R^1$ is a 2-(lower alkylthio)-1-hydroxyethyl group, by treating it with an alkali metal lower alkylsulfide. In this case, when $R^3$ is an esterified carboxyl-lower alkyl group, said group is hydrolyzed at the same time to be converted into a carboxy-lower alkyl group.

The desired compound (I) in which $R^2$ is a N-lower alkoxycarbonyl-substituted nitrogen-containing heteromonocyclic group or nitrogen-containing heterobicyclic group can be converted into a desired compound in which $R^2$ is a N-non-substituted nitrogen-containing heteromonocyclic group or nitrogen-containing heterobicyclic group, by carrying out deacylation in the same manner as in Method (b). Further, by carrying out treatment with a mixed acid anhydride obtained from formic acid and acetic acid anhydride or with a cyano-lower alkane (acrylonitrile, etc.), N-position of the nitrogen-containing heteromonocyclic group or nitrogen-containing heterobicyclic group can be formylated or cyano-lower alkylated.

The desired compound (I) in which $R^3$ is a cyano-lower alkyl group can be converted into a corresponding tetrazole compound by treating it with tributyltin azide ($Bu_3SnN_3$) or can be converted into a corresponding lower alkoxycarbonyl compound by treating it with an acid in a lower alkanol.

The desired compound (I) in which a lower alkoxy group exists in at least one of the substituents of Ring A, $R^1$, $R^2$ and $R^3$ can be converted into a corresponding hydroxy compound by treating it with a Lewis acid such as boron tribromide, etc. and can be further converted into a lower alkoxy compound by treating it with a lower alkyl halide or the like.

The desired compound (I) in which Y is a lower alkenylene can be converted into a desired compound in which Y is a lower alkylene group by reduction.

All of the mutually converting reactions of the desired compounds described above proceed without racemization so that when an optically active isomer is used as a starting material, an optically active desired compound can be obtained.

The 2-oxoindoline derivatives prepared by the above preparation processes can be isolated from the reaction mixtures according to the conventional method after completion of the reactions and can be purified according to the conventional method, if desired. For example, after completion of the reaction, if necessary, after an excessive reagent is decomposed or a reaction solvent is removed, the desired compound can be collected by extraction with a soluble solvent or precipitation by adding a suitable solvent. Further, it can be purified by column chromatography, recrystallization, etc., if necessary.

The amine compound (II) which is a starting material of the present invention can be prepared by, if desired, after introducing a group: —Q—$R^1$ (where Q and $R^1$ have the same meanings as described above.) into the amino group of a compound represented by the formula (VI):

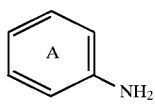

(VI)

(wherein Ring A has the same meaning as described above.), reacting the compound with an oxalyl halide, treating the resulting compound represented by the formula (VII):

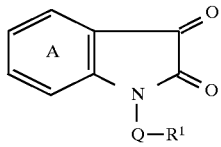

(VII)

(wherein Ring A, $R^1$ and Q have the same meanings as described above.), with hydroxyamine and then reducing it to obtain a compound represented by the formula (VIII):

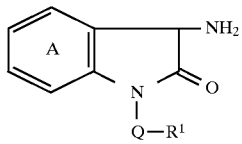

(VIII)

(wherein Ring A, $R^1$ and Q have the same meanings as described above.), if desired, protecting the amino group thereof and reacting the compound with an alkylating agent in the same manner as in Method (B) and removing the protective group when the amino group is protected.

The compound (VII) which is 4-(lower alkoxy)-2,3-dihydro-1H-indole-2,3-dione can be prepared by converting a 3-(lower alkoxy)aniline into a 3'-(lower alkoxy)-2,2-dimethylpropionanilide according to the method described in the literature [R. M. Soil et al., J. Org. Chem., 53, 2844 (1988)], lithiating the ortho position of said anilide compound and then subjecting it to treatment with diethyl oxalate and further to cyclization (ring closure).

The compound (VIII) in which Q is a lower alkylene group can be also prepared by introducing a group: —$Q^2$—$R^1$ (where $Q^2$ represents a lower alkylene group, and $R^1$ has the same meaning as described above.) to nitrogen atom at 1-position of the indoline ring of the compound (VIII) in which the group: —Q—$R^1$ is hydrogen atom, in the same manner as in Method (a).

The starting compound (IV) can be prepared by reacting the compound (VIII) with the compound (III) in the same manner as in Method (A).

The starting compound represented by the formula:

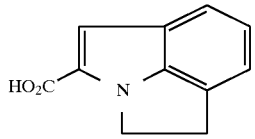

can be prepared by hydrolyzing a compound represented by the formula:

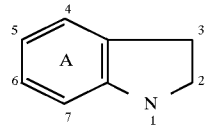

[H. Rapoport et al., J. Am. Chem. Soc., 80, 5574 (1958)] in the same manner as in Method (b).

The desired compound (I) which is an optically active isomer can be prepared by reacting the optically active amine compound (II) or a salt thereof with the carboxylic acid compound (III), a reactive derivative thereof or a salt thereof.

The optically active isomer of the amine compound (II) can be obtained by forming an optical resolution agent and a diastereomer salt from the racemic amine compound (II) according to the conventional method and carrying out optical resolution. As the optical resolution agent, there may be used a conventionally used resolution agent, for example, optically active dibenzoyl tartaric acid can be used.

In the present specification, the lower alkyl group and the lower alkoxy group mean those having 1 to 6 carbon atoms, preferably those having 1 to 4 carbon atoms. The lower alkanoyl group means one having 2 to 6 carbon atoms, preferably one having 2 to 4 carbon atoms. The cycloalkyl group means one having 3 to 9 carbon atoms, preferably one having 3 to 6 carbon atoms. The lower alkylene group means one having 1 to 8 carbon atoms, preferably one having 1 to 5 carbon atoms. The lower alkenylene group means one having 2 to 6 carbon atoms, preferably one having 2 to 4 carbon atoms. The halogen atom includes chlorine, bromine, fluorine and iodine, preferably chlorine and fluorine.

Further, in the formulae (I), (II), (IV), (VII) and (VIII), when the substitution position of the substituent on Ring A is specified, it is specified by the following position number of the indoline ring.

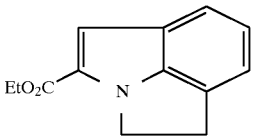

EXAMPLES

In the following, the present invention is described in more detail by referring to Reference examples and Examples, but the present invention is not limited thereby.

Example 1

(1) Under argon atmosphere and ice cooling, a solution of 2.80 g of 3,4-dichlorobenzoyl chloride in 20 ml of methylene chloride was added dropwise to a mixture of 2.84 g of 3-amino-1-pentyl-2,3-dihydro-1H-indol-2-one hydrochloride, 2.24 g of sodium hydrogen carbonate, 30 ml of chloroform and 30 ml of water. The reaction mixture was stirred under ice cooling for 30 minutes and then at room temperature for 30 minutes, diluted with water and extracted with chloroform. After the chloroform layer was washed and dried, the solvent was removed by evaporation. The residue was recrystallized from ethyl acetate-hexane to afford 4.06 g of 3,4-dichloro-N-(2,3-dihydro-2-oxo-1-pentyl-1H-indol-3-yl)benzamide as colorless crystals. Melting point: 125° to 126° C., IR (Nujol) (cm$^{-1}$): 3280, 1725, 1635, 1610, MS (m/z): 390 (M$^+$), 374, 372, 217 (base).

(2) Under argon atmosphere, a mixture of 3.56 g of the product obtained above, 4.1 ml of methyl acrylate, 3.82 g of potassium carbonate and 70 ml of acetone was stirred at room temperature overnight. Insolubles were removed by filtration, and the filtrate was concentrated under reduced pressure. The residue was dissolved in chloroform, and the extract was washed and dried. After removal of solvent, the resulting crude crystals were recrystallized from ethyl acetate-hexane to afford 3.96 g of methyl 3-[3-(3,4-dichlorobenzoylamino)-2,3-dihydro-2-oxo-1-pentyl-1H-indol-3-yl]propionate, i.e., 3-(3,4-dichlorobenzoylamino)-3-(2-methoxycarbonylethyl)-1-pentyl-1H-indol-2(3H)-one as colorless crystals. Melting point: 84° to 114° C., IR (Nujol) (cm$^{-1}$) : 3330, 1735, 1705, 1660, MS (m/z): 476 (M$^+$) , 173 (base).

Example 2

(1) Under argon atmosphere and ice cooling, a solution of 16.5 g of triethylamine in 50 ml of methylene chloride was added dropwise to a stirred mixture of 15.05 g of 3-amino-2,3-dihydro-1H-indol-2-one hydrochloride and 17.20 g of 3,4-dichlorobenzoyl chloride suspended in 300 ml of methylene chloride. The mixture was stirred at room temperature for 30 minutes. The reaction mixture was treated with 100 ml of water, and the whole was stirred for additional 2 hours. The resulting precipitates were collected by filtration, washed and then recrystallized from dimethylformamide-water to afford 22.9 g of 3,4-dichloro-N-(2,3-dihydro-2-oxo-1H-indol-3-yl)benzamide as colorless needle crystals. Melting point: 283° to 285° C. (decomposed), IR (Nujol) (cm$^{-1}$) : 3280, 3160, 3100, 1710, 1690, 1635, MS (m/z): 322 & 320 (M$^+$), 147 (base).

(2) Under argon atmosphere and ice cooling, 10 g of potassium carbonate was added to a stirred solution of 23.0 g of the product obtained above and 7.52 g of ethyl acrylate in dimethyl sulfoxide (130 ml). The mixture was stirred at room temperature for 1 hour and then diluted with ice water. The resulting precipitates were collected by filtration and crystallized from ethyl acetate-hexane to afford 26.33 g of ethyl 3-[3-(3,4-dichlorobenzoylamino)-2,3-dihydro-2-oxo-1H-indol-3-yl]propionate as colorless powder. Melting point: 227° to 228° C., IR (Nujol) (cm$^{-1}$): 3350, 3320, 3280, 1740, 1710, 1655, 1625, MS (m/z): 422 & 420 (M$^+$).

Example 3

(1) Under ice cooling, 1.10 g of 1-(3-dimethylaminopropyl)-3-ethylcarbodiimide hydrochloride was added to a stirred mixture of 1.22 g of 3-amino-2,3-dihydro-1-pentyl-1H-indol-2-one hydrochloride, 0.93 g of 1,2,3,4-tetrahydronaphthalene-2-carboxylic acid, 0.72 g of 1-hydroxybenzotriazole and 40 ml of methylene chloride. After the reaction mixture was stirred under ice cooling for 1 hour, 1.0 ml of triethylamine was added to the mixture. The resulting mixture was stirred under ice cooling for 2 hours and then stirred at room temperature for 2 hours. The solvent was removed by evaporation under reduced pressure. The residue was extracted with ethyl acetate, and the extract was washed and dried. After removal of solvent, the residual solid was recrystallized from ethyl acetate-hexane to afford 1.36 g of N-(2,3-dihydro-2-oxo-1-pentyl-1H-indol-3-yl)-1,2,3,4-tetrahydronaphthalene-2-carboxamide as colorless crystals. Melting point: 127° to 132° C., IR (Nujol) (cm$^{-1}$): 3280, 1725, 1640, 1610, MS (m/z): 376 (M$^+$), 218 (base), 147, 31.

(2) The product obtained above was treated in the same manner as in Example 1-(2) to afford methyl 3-[2,3-dihydro-2-oxo-1-pentyl-3-(1,2,3,4-tetrahydro-2-naphthylcarbonylamino)-1H-indol-3-yl]propionate. Melting point: 172° to 179° C.

Example 4

Under argon atmosphere, a mixture of 2.70 g of 3,4-dichloro-N-(2,3-dihydro-2-oxo-1-pentyl-1H-indol-3-yl) benzamide, 1.30 g of acrylonitrile, 30 ml of acetone and 1.46 g of potassium carbonate was stirred at room temperature for 1 hour. After removal of solvent, the residue was treated with water and extracted with ethyl acetate. After the ethyl acetate extract was washed and dried, the solvent was removed by evaporation. The residue was crystallized from ethyl acetate-hexane to afford 2.28 g of 3,4-dichloro-N-[3-(2-cyanoethyl)-2,3-dihydro-2-oxo-1-pentyl-1H-indol-3-yl]-benzamide as colorless crystals. Melting point: 79° to 84° C., IR (Nujol) (cm$^{-1}$): 3340, 2325, 1700, 1655, 1610, MS (m/z): 445 & 443 (M$^+$).

Example 5

Under ice cooling, 0.98 ml of triethylamine was added dropwise to a stirred mixture of 1 g of 3-amino-2,3-dihydro-6-methoxy-1-pentyl-1H-indol-2-one hydrochloride, 683 mg of β-naphthylcarbonyl chloride and 15 ml of methylene chloride. The mixture was stirred at room temperature for 1 hour. The reaction mixture was diluted with chloroform, and the chloroform extract was washed with water and dried. After removal of solvent, the residue was dissolved in 10 ml of dimethyl sulfoxide, and 0.38 ml of ethyl acrylate and 500 mg of potassium carbonate were added to this mixture. The whole mixture was stirred at room temperature for 30 minutes under argon atmosphere. The reaction mixture was treated with water and extracted with ethyl acetate. The ethyl acetate extract was washed with water and dried. After removal of solvent, the residue was crystallized from ethyl acetate-hexane to afford 1.55 g of ethyl 3-[2,3-dihydro-6-methoxy-3-(2-naphthalenecarbonyl)amino-2-oxo-1-pentyl-1H-indol-3-yl)propionate. Melting point: 156° to 159° C., IR (Nujol) (cm$^{-1}$): 3260, 1735, 1690, 1650, 1620, MS (m/z): 502 (M$^+$), 45.

Example 6

Under ice cooling, 680 mg of 1-(3-dimethylaminopropyl)-3-ethylcarbodiimide hydrochloride, 480 mg of 1-hydroxybenzotriazole and 0.73 ml of triethylamine were added to a mixture of 1 g of 3-amino-2,3-dihydro-6-methoxy-1-pentyl-1H-indol-2-one hydrochloride, 570 mg of indole-2-carboxylic acid and 20 ml of methylene chloride. The mixture was stirred at room temperature for 2.5 hours. The reaction mixture was treated with water and extracted with ethyl acetate. The ethyl acetate extract was washed with water and dried. After removal of solvent, the residue was dissolved in 10 ml of dimethyl sulfoxide, and 0.38 ml of ethyl acrylate and 485 mg of potassium carbonate were added to this mixture. The whole mixture was stirred at room temperature for 1.5 hours. The reaction mixture was treated with water and extracted with ethyl acetate. The ethyl acetate extract was washed with water and dried, and evaporated in vacuo to afford 1.72 g of ethyl 3-[2,3-dihydro-3-(1H-indol-2-ylcarbonyl)amino-6-methoxy-2-oxo-1-pentyl-1H-indol-3-yl]propionate.

Example 7

(1) To a stirred suspension of 2.00 g of 3-amino-1-(4-fluorophenyl)-2,3-dihydro-6-methoxy-1H-indol-2-one hydrochloride, 1.33 g of sodium isoquinoline-3-carboxylate and 0.88 g of 1-hydroxybenzotriazole in 10 ml of anhydrous dimethylformamide was added 1.49 g of 1-(3-dimethylaminopropyl)-3-ethylcarbodiimide hydrochloride under ice cooling. The whole was stirred for 30 minutes. The reaction mixture was extracted by pouring a mixed solvent of ethyl acetate-tetrahydrofuran (2:1). The extract was washed with water, dried and evaporated. The residue was triturated with a mixed solvent of ethyl acetate and tetrahydrofuran to afford 2.60 g of N-[1(4-fluorophenyl)-2,3-dihydro-6-methoxy-2-oxo-1H-indol-3-yl]-3-isoquinolinecarboxamide as a powder. Melting point: 219° to 220° C.

(2) Under argon atmosphere, 195 mg of potassium carbonate was added to a mixture of 200 mg of the product obtained above, 275 mg of ethyl 4-bromobutyrate and 4 ml of dimethylformamide. The mixture was stirred at room temperature for 15 hours. For quenching excess reagent, 71 mg of thiourea was added to the mixture, and the resulting mixture was stirred for 24 hours. The reaction mixture was poured into water and extracted with ethyl acetate. The extract was washed with water and dried, and the solvent was removed by evaporation. The residue was purified by silica gel column chromatography [hexane-ethyl acetate (2:1)] to afford 140 mg of ethyl 4-[1-(4-fluorophenyl)-2,3-dihydro-3-(3-isoquinolinylcarbonylamino)-6-methoxy-2-oxo-1H-indol-3-yl]butyrate as a caramel. IR (Nujol) (cm$^{-1}$): 3380, 1740, 1675, 1625, MS (m/z): 541 (M$^+$), 476, 426, 156, 128 (base).

Examples 8 to 42

By treating the corresponding starting compounds in the same manner as described in either of Examples 1 to 7, the compounds in Table 1 to Table 6 were obtained.

TABLE 1

| Example No. | R$^3$ | -Y-R$^2$ | Physical constant, etc. |
|---|---|---|---|
| 8 | CH$_2$CH$_2$CO$_2$CH$_3$ | naphthyl | Foamy product |
| 9 | CH$_2$CH$_2$CO$_2$C$_2$H$_5$ | 2-methylindol-5-yl | M.P.: 142–144° C. |
| 10 | CH$_2$CH$_2$CO$_2$C$_2$H$_5$ | 2-methyl-1,2,3,4-tetrahydroisoquinolin-6-yl | Oily product |
| 11 | CH$_2$CH$_2$CO$_2$CH$_3$ | quinolin-6-yl | Foamy product |
| 12 | CH$_2$CH$_2$CO$_2$CH$_3$ | isoquinolin-6-yl | Oily product |
| 13 | CH$_2$CH$_2$CO$_2$C$_2$H$_5$ | (E)-2-(3-methoxyphenyl)ethenyl | M.P.: 135–136° C. |
| 14 | CH$_2$CH$_2$CO$_2$C$_2$H$_5$ | 2-(tert-butoxycarbonyl)-1,2,3,4-tetrahydroisoquinolin-6-yl | Caramel |

TABLE 2

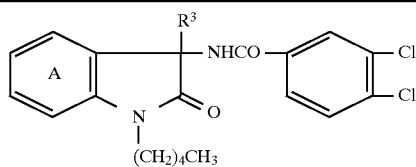

| Example No. | Ring A | $R^3$ | Physical constant, etc. |
|---|---|---|---|
| 15 | 2-OCH$_3$, 3-methyl phenyl | CH$_2$CH$_2$CO$_2$CH$_3$ | M.P.: 166–168° C. |
| 16 | 4-CH$_3$O, 3-methyl phenyl | CH$_2$CH$_2$CO$_2$CH$_3$ | M.P.: 138–139° C. |
| 17 | 4-CH$_3$O, 3-methyl phenyl | CH$_2$CH$_2$CO$_2$C$_2$H$_5$ | M.P.: 172–174° C. |
| 18 | 2,3-dimethyl, 1-OCH$_3$ phenyl | CH$_2$CH$_2$CO$_2$CH$_3$ | M.P.: 167–168° C. |

TABLE 3

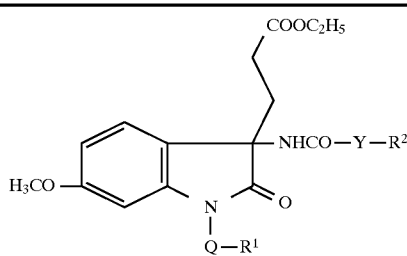

| Example No. | -Q-R$^1$ | -Y-R$^2$ | Physical constant, etc. |
|---|---|---|---|
| 19 | —(CH$_2$)$_4$CH$_3$ | isoquinolinyl | Foamy product |
| 20 | —(CH$_2$)$_4$CH$_3$ | quinolinyl | M.P.: 281–282.5° C. |
| 21 | —(CH$_2$)$_4$CH$_3$ | quinolinyl | Foamy product |
| 22 | phenyl | naphthyl | Oily product |

TABLE 3-continued

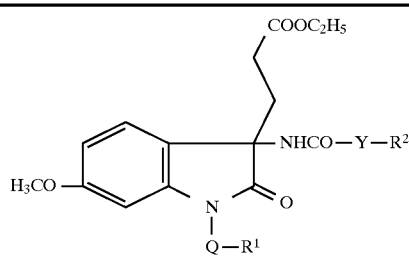

| Example No. | -Q-R$^1$ | -Y-R$^2$ | Physical constant, etc. |
|---|---|---|---|
| 23 | 2-F phenyl | naphthyl | M.P.: 186–186.5° C. |
| 24 | 4-F phenyl | naphthyl | Oily product |
| 25 | 2-F phenyl | isoquinolinyl | M.P.: 96–97° C. |

TABLE 4
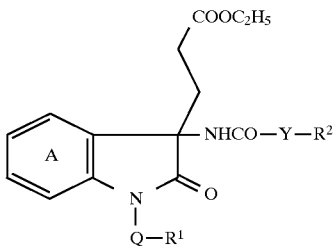
| Example No. | Ring A | -Q-R¹ | -Y-R² | Physical constant, etc. |
|---|---|---|---|---|
| 26 | 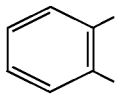 | 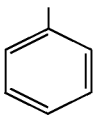 | 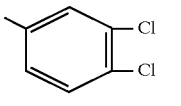 | M.P.: 200–201° C. |
| 27 | 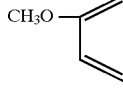 | 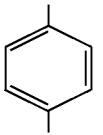 | 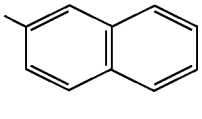 | M.P.: 183° C. |
| 28 | 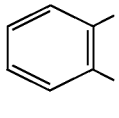 | 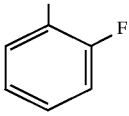 | 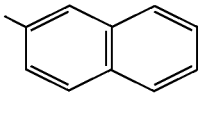 | M.P.: 166–167° C. |
| 29 | 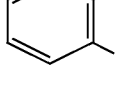 | 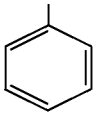 | 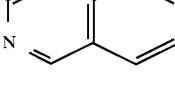 | Oily product |
| 30 | 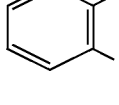 | 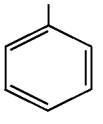 | 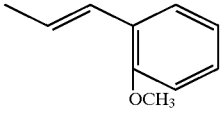 | M.P.: 181–183° C. |
| 31 | 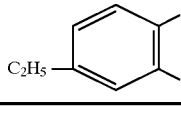 | —(CH₂)₄CH₃ | 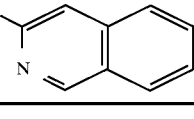 | Oily product |

TABLE 5

Structure: 6-methoxy-indolin-2-one with COOC₂H₅-CH₂CH₂- and NHCO—Y—R² substituents at the 3-position, and Q—R¹ on the nitrogen.

| Example No. | -Q-R¹ | -Y-R² | Physical constant, etc. |
|---|---|---|---|
| 32 | 2-fluorophenyl | 2-methylindol-yl (NH) | M.P.: 234–238° C. |
| 33 | 4-fluorophenyl | 2-methylisoquinolinyl | Oily product |
| 34 | 4-fluorophenyl | 2-methylindol-yl (NH) | M.P.: 140–146° C. |
| 35 | 3-chlorophenyl | 2-methylisoquinolinyl | Oily product |
| 36 | cyclohexyl | 2-methylisoquinolinyl | M.P.: 212–214° C. |

TABLE 6

Structure: 6-methoxy-indolin-2-one with R³ and NHCO—Y—R² at the 3-position, and Q—R¹ on the nitrogen.

| Example No. | R³ | -Q-R¹ | -Y-R² | Physical constant, etc. |
|---|---|---|---|---|
| 37 | CH₂CH₂CO₂C₂H₅ | cyclohexyl | 2-methylindol-yl (NH) | M.P.: 212–214° C. |
| 38 | CH₂CH₂CO₂C₂H₅ | cyclopentyl | 2-methylisoquinolinyl | Foamy product |
| 39 | CH₂CH₂CO₂C₂H₅ | cyclopentyl | 2-methylindol-yl (NH) | M.P.: 178–180° C. |

TABLE 6-continued

Structure:

$H_3CO$-[benzene fused to indolinone]-$R^3$, with NHCO—Y—$R^2$ on C3, and N—Q—$R^1$ on ring N, C=O

| Example No. | $R^3$ | -Q-$R^1$ | -Y-$R^2$ | Physical constant, etc. |
|---|---|---|---|---|
| 40 | $CH_2CH_2CO_2C_2H_5$ | 3-ethylphenyl ($C_2H_5$) | isoquinolin-3-yl | Oily product |
| 41 | $CH_2CH_2CO_2C_2H_5$ | 3-methoxyphenyl ($OCH_3$) | isoquinolin-3-yl | Oily product |
| 42 | $CH_2CO_2CH_3$ | 4-fluorophenyl (F) | isoquinolin-3-yl | Foamy product |

Example 43

(1) Under argon atmosphere, 0.85 ml of ethyl acrylate and 1.94 g of potassium carbonate were added to 2.00 g of 3-amino-2,3-dihydro-6-methoxy-2-oxo-1-pentyl-1H-indole hydrochloride dissolved in 40 ml of dimethyl sulfoxide, the mixture was stirred at room temperature for 3 hours. The reaction mixture was extracted with ethyl acetate, and the extract was washed and dried. Insolubles were removed by filtration, and the filtrate was concentrated. The residue was purified by silica gel column chromatography [chloroform-ethyl acetate (1:1)] to afford 1.36 g of ethyl 3-[3-amino-2,3-dihydro-6-methoxy-2-oxo-1-pentyl-1H-indol-3-yl]-propionate as a pale yellow oily product.

(2) The product obtained above and 5,6-dihydro-4H-pyrrolo-[3,2,1-ij]quinoline-2-carboxylic acid were treated in the same manner as described in Example 3-(1) to afford ethyl 3-{3-[(5,6-dihydro-4H-pyrrolo[2,3,1-ij]quinolin-2-yl)-carbonyl]amino-2,3-dihydro-6-methoxy-2-oxo-1-pentyl-1H-indol-3-yl}propionate.

Examples 44 to 60

By treating the corresponding starting compounds in the same manner as described in Example 43, the compounds in Table 7 to Table 9 were obtained.

TABLE 7
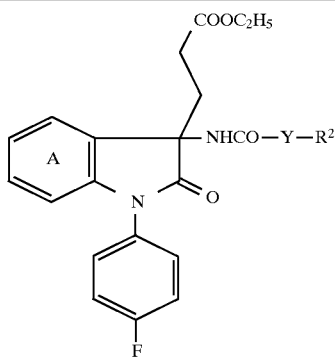
| Example No. | Ring A | -Y-R² | Physical constant, etc. |
|---|---|---|---|
| 44 | CH₃O-phenyl | 2-(1,2,3,4-tetrahydroquinolinyl) | M.P.: 174–175° C. |
| 45 | CH₃O-phenyl | 3-quinolinyl | M.P.: 191–194° C. |
| 46 | CH₃O-phenyl | 3-isoquinolinyl | Oily product |
| 47 | CH₃O-phenyl | 2-(2,3-dihydro-1H-pyrrolizinyl) | M.P.: 200–203° C. |
| 48 | C₂H₅-phenyl | 3-isoquinolinyl | Amorphous |
TABLE 8
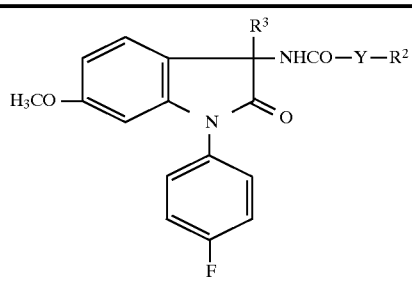
| Example No. | R³ | -Y-R² | Physical constant, etc. |
|---|---|---|---|
| 49 | CH₂CH₂CO₂C₂H₅ | benzo[b]thiophen-2-yl | M.P.: 172–173° C. |

TABLE 8-continued

[Structure: 6-methoxy indolin-2-one with R³ and NHCO-Y-R² substituents at 3-position, N-substituted with 4-fluorophenyl]

| Example No. | R³ | -Y-R² | Physical constant, etc. |
|---|---|---|---|
| 50 | CH₂CH₂CO₂C₂H₅ | 2-(1H-benzimidazolyl) | M.P.: 203–204° C. |
| 51 | CH₂CH₂CO₂C₂H₅ | 2-benzofuranyl | M.P.: 151–153° C. |
| 52 | CH₂CH₂CO₂C₂H₅ | 5-indolyl | M.P.: 181° C. |
| 53 | CH₂CH₂CO₂C₂H₅ | 3-coumarinyl | M.P.: 123–125° C. |
| 54 | CH₂CH₂CN | 3-isoquinolinyl | M.P.: 165–166° C. |

TABLE 9

[Structure: 6-methoxy indolin-2-one with COOC₂H₅-containing chain (CH₂CH₂COOC₂H₅) and NHCO-Y-R² at 3-position, N-substituted with 4-fluorophenyl]

| Example No. | -Y-R² | Physical constant, etc. |
|---|---|---|
| 55 | 1-naphthyl | M.P.: 150–152° C. |
| 56 | 5-benzimidazolyl | Amorphous |

TABLE 9-continued

[Structure: indoline with H3CO group, COOC2H5 side chain, NHCO-Y-R² substituent, N-(4-fluorophenyl)]

| Example No. | -Y-R² | Physical constant, etc. |
|---|---|---|
| 57 | [quinoxaline-CH2-] | Oily product |
| 58 | [indoline methyl structure] | Amorphous |
| 59 | [2-naphthyl-CH2CH2-] | M.P.: 209–210.5° C. |
| 60 | [2-pyridyl-CH2CH2-] | Caramel |

Example 61

A mixture of 1.06 g of ethyl 3-[3-(3,4-dichlorobenzoylamino)-2,3-dihydro-2-oxo-1H-indol-3-yl]propionate, 1.0 g of 3-phenylpropyl bromide, 1.10 g of potassium carbonate and 16 ml of acetone was refluxed overnight. The solvent was removed by evaporation. The residue was extracted with ethyl acetate, washed with water and dried. After removal of solvent, the residual solid was crystallized from isopropyl ether-hexane to afford 1.25 g of ethyl 3-[3-(3,4-dichlorobenzoylamino)-2,3-dihydro-2-oxo-1-(3-phenylpropyl)-1H-indol-3-yl]propionate as a colorless solid. Melting point: 119.5° to 121.5° C., IR (Nujol) (cm$^{-1}$): 3320, 1730, 1700, 1660, 1615, FAB-MS (m/z): 541 & 539 (MH$^+$).

Examples 62 to 74

By treating the corresponding starting compounds in the same manner as described in Example 61, the compounds in Table 10 and Table 11 were obtained.

TABLE 10

[Structure: indoline with COOC2H5 side chain, NHCO-(3,4-dichlorophenyl), N-Q-R¹]

| Example No. | -Q-R¹ | Physical constant, etc. |
|---|---|---|
| 62 | [-CH2CH2CH2-phenyl] | M.P.: 145–147° C. |
| 63 | [-CH2CH2CH2-morpholine] | M.P.: 143–144° C. |
| 64 | [-CH2CH2-(4-pyridyl)] | Caramel |
| 65 | $-(CH_2)_3CN$ | M.P.: 89° C. |
| 66 | $-(CH_2)_3OCH_3$ | M.P.: 100–101.5° C. |
| 67 | $-(CH_2)_2SCH_3$ | M.P.: 140–140.5° C. |
| 68 | $-CH_2CO_2C(CH_3)_3$ | M.P.: 166.5–167.5° C. |

TABLE 11

[Structure: indoline with COOC2H5 side chain, NHCO-(3,4-dichlorophenyl), N-Q-R¹]

| Example No. | -Q-R¹ | Physical constant, etc. |
|---|---|---|
| 69 | [-CH2-cyclopropyl] | M.P.: 158–159° C. |
| 70 | $-(CH_2)_5CH_3$ | M.P.: 91–91.5° C. |
| 71 | $-(CH_2)_4-$phenyl | Oily product |
| 72 | [-CH2CH2-(3-methoxyphenyl)] | M.P.: 122.5–123° C. |
| 73 | [-CH2-tetrahydrofuranyl] | M.P.: 155–156° C. |

TABLE 11-continued

[Structure: indol-2-one core with COOC₂H₅ propyl chain, NHCO linkage to 3,4-dichlorophenyl, and N-Q-R¹ substituent]

| Example No. | -Q-R¹ | Physical constant, etc. |
|---|---|---|
| 74 | —(CH₂)₃SCH₃ | M.P.: 116.5–119° C. |

Example 75

1.22 g of m-chloroperbenzoic acid was added to a stirred solution of 2.05 g of ethyl 3-[3-(3,4-dichlorobenzoylamino)-2,3-dihydro-1-(3-methylthiopropyl)-2-oxo-1H-indol-3-yl]propionate in chloroform (80 ml) under ice cooling. The mixture was stirred at room temperature overnight. After removal of solvent, the residue was extracted with ethyl acetate. The extract was washed with water, dried, and evaporated to dryness under reduced pressure. The residue was separated by silica gel column chromatography [ethyl acetate-hexane (1:2) to chloroform-methanol (20:1)] to afford ethyl 3-[3-(3,4-dichlorobenzoylamino)-2,3-dihydro-1-(3-methylsulfinylpropyl)-2-oxo-1H-indol-3-yl]propionate (a sulfinyl compound, Rf: small) and ethyl 3-[3-(3,4-dichlorobenzoylamino)-2,3-dihydro-1-(3-methylsulfonylpropyl)-2-oxo-1H-indol-3-yl]propionate (a sulfonyl compound, Rf: large). The sulfinyl compound was recrystallized from ethyl acetate-isopropyl ether to afford 1.07 g of the sulfinyl compound as colorless prism. Melting point: 154° to 159° C., IR (Nujol) (cm⁻¹): 3220, 1720, 1655, 1610, FAB-MS (m/z): 527 & 525 (MH⁺).

Example 76

Ethyl 3-[3-(3,4-dichlorobenzoylamino)-2,3-dihydro-1-(3-methylsulfonylpropyl)-2-oxo-1H-indol-3-yl]propionate (a sulfonyl compound, Rf: large) obtained by separation by silica gel column chromatography in Example 75 was recrystallized from ethyl acetate-hexane to afford 592 mg of the sulfonyl compound as colorless needles. Melting point: 106° to 108° C., IR (Nujol) (cm⁻¹): 3360, 1730, 1660, 1615, FAB-MS (m/z): 543 & 541 (MH⁺).

Example 77

5 ml of trifluoroacetic acid was added to a solution of 700 mg of ethyl 3-[1-(t-butoxycarbonylmethyl)-3-(3,4-dichlorobenzoylamino)-2,3-dihydro-2-oxo-1H-indol-3-yl]propionate in methylene chloride (20 ml). The mixture was stirred at room temperature for 3 hours. The reaction mixture was evaporated to dryness under reduced pressure. The residue was recrystallized from ethyl acetate-hexane to afford 651 mg of 2-[3-(3,4-dichlorobenzoylamino)-2,3-dihydro-3-(2-ethoxycarbonylethyl)-2-oxo-1H-indol-1-yl] acetic acid as colorless prism crystals. Melting point: 219° to 220° C., IR (Nujol) (cm⁻¹): 3280, 1735, 1720, 1705, 1670, 1610, FAB-MS (m/z): 481 & 479 (MH⁺).

Example 78

(1) 2.5 ml of boron tribromide was added dropwise to a stirred solution of 2.37 g of ethyl 3-[2,3-dihydro-6-methoxy-3-(2-naphthalenecarbonyl)amino-2-oxo-1-phenyl-1H-indol-3-yl]propionate in methylene chloride (20 ml) under ice cooling. The mixture was stirred at room temperature for 1 hour. The reaction mixture was poured into ice water and extracted with ethyl acetate. The extract was evaporated to dryness under reduced pressure to afford ethyl 3-[2,3-dihydro-6-hydroxy-3-(2-naphthalenecarbonyl)amino-2-oxo-1-phenyl-1H-indol-3-yl]propionate.

(2) 330 mg of 63.3% sodium hydride was added to a stirred of a solution of 2.15 g of the product obtained above in dimethylformamide (20 ml). After the mixture was stirred, 0.35 ml of ethyl iodide was added to the mixture. The resulting mixture was stirred at room temperature for 2.5 hours. The reaction mixture was treated with water and extracted with ethyl acetate. The ethyl acetate extract was washed with water, dried, and the solvent was removed by evaporation. The residue was purified by silica gel column chromatography [ethyl acetate-hexane (1:2)] to afford 928 mg of ethyl 3-[6-ethoxy-2,3-dihydro-3-(2-naphthalenecarbonyl)amino-2-oxo-1-phenyl-1H-indol-3-yl]-propionate as colorless needles. Melting point: 195° to 196° C., IR (Nujol) (cm⁻¹): 3420, 1750, 1730, 1640, 1620, 1540, MS (m/z): 522 (M⁺), 155 (base).

Example 79

Under ice cooling, a hydrochloric acid gas was passed through a stirred solution of 6.79 g of ethyl 3-[3-(2-t-butoxycarbonyl-1,2,3,4-tetrahydro-3-isoquinolinyl)-carbonylamino-2,3-dihydro-2-oxo-1-pentyl-1H-indol-3-yl]-propionate in ethyl acetate (75 ml) until the gas was saturated. The mixture was stirred at 0° C. for 2.5 hours. After removal of solvent, the residue was triturated in isopropyl ether to afford 6.05 g of ethyl 3-[2,3-dihydro-2-oxo-1-pentyl-3-(1,2,3,4-tetrahydro-3-isoquinolinyl)-carbonylamino-1H-indol-3-yl]propionate hydrochloride as a pale yellow amorphous solid. IR (Nujol) (cm⁻¹): 3180, 1725, 1690, 1610, FAB-MS (m/z): 478 (MH⁺), 132 (base).

Example 80

A mixture of 0.66 g of formic acid and 1.35 g of acetic acid anhydride was heated at 50° C. for 15 minutes. After cooling by dilution with 15 ml of anhydrous methylene chloride, 0.68 g of sodium formate and 15 ml of a methylene chloride solution of 1.70 g of ethyl 3-[2,3-dihydro-2-oxo-1-pentyl-3-(1,2,3,4-tetrahydro-3-isoquinolinyl) carbonylamino-1H-indol-3-yl]propionate were added to this mixed anhydride solution. The whole was stirred at room temperature overnight. The reaction mixture was neutralized with an aqueous saturated sodium hydrogen carbonate solution and then extracted with chloroform. The extract was washed, dried, filtered and then evaporated in vacuo to afford 1.72 g of ethyl 3-[3-(2-formyl-1,2,3,4-tetrahydro-3-isoquinolinyl)carbonylamino-2,3-dihydro-2-oxo-1-pentyl-1H-indol-3- yl]propionate as a pale yellow amorphous solid. IR (Nujol) (cm⁻¹): 3280, 1720, 1655, 1610, FAB-MS (m/z): 506 (MH⁺) 160 (base).

Example 81

Under ice cooling, 2 ml of boron tribromide was added dropwise to a stirred solution of 1.64 g of ethyl 3-[2,3-dihydro-3-[(E)-3-(3-methoxyphenyl)-2-propenoylamino]-2-oxo-1-pentyl-1H-indol-3-yl]propionate in methylene chloride (30 ml). After stirring under ice cooling for 1 hour, the mixture was poured into ice water and extracted with chloroform. After the extract was dried, the solvent was removed by evaporation under reduced pressure. The residue was purified by silica gel column chromatography [hexane-ethyl acetate (1:1)] to afford 1.53 g of ethyl 3-[2,3-dihydro-3-[(E)-3-(3-hydroxyphenyl)-2-propenoylamino]-2-oxo-1-pentyl-1H-indol-3-yl]propionate as a colorless amorphous solid. IR (Nujol) (cm$^{-1}$) : 3280, 1705, 1660, 1610, FAB-MS (m/z): 465 (MH$^+$), 302, 256, 228, 147 (base).

Example 82

Ethyl 3-[2,3-dihydro-3-[(E)-3-(2-methoxyphenyl)-2-propenoylamino]-2-oxo-1-phenyl-1H-indol-3-yl]propionate was treated in the same manner as in Example 81 to afford ethyl 3-[2,3-dihydro-3-[(E)-3-(2-hydroxyphenyl)-2-propenoyl-amino]-2-oxo-1-phenyl-1H-indol-3-yl] propionate as a colorless solid. IR (Nujol) (cm$^{-1}$): 3280, 1740, 1710, 1610, FAB-MS (m/z): 470 (M$^+$), 91.

Example 83

12 ml of an aqueous 15% sodium methyl sulfide solution was added to 24 ml of an ethanol solution of 1.635 g of ethyl 3-[3-(3,4-dichlorobenzoylamino)-2,3-dihydro-1-(2-oxiranylmethyl)-2-oxo-1H-indol-3-yl]propionate. The mixture was stirred at 50° C. for 3 hours. The reaction mixture was concentrated, made acidic with aqueous 10% hydrochloric acid and extracted with ethyl acetate. The extract was washed, dried, filtered and then concentrated. The residue was purified by silica gel column chromatography [chloroform-methanol (10:1)] and recrystallized from ethyl acetate-hexane to afford 1.52 g of 3-[3-(3,4-dichlorobenzoylamino)-2,3-dihydro-1-(3-methylthio-2-hydroxypropyl)-2-oxo-1H-indol-3-yl]propionic acid as colorless needles. Melting point: 168.5° to 169.5° C., IR (Nujol) (cm$^{-1}$): 3400, 3300, 1710, 1650, 1615, FAB-MS (m/z): 499 & 497 (MH$^+$).

Example 84

A mixture of 719 mg of ethyl 3-[2,3-dihydro-3-[(E)-3-(2-methoxyphenyl)-2-propenoylamino]-2-oxo-1-phenyl-1H-indol-3-yl]propionate, 20 ml of ethanol and 6 ml of tetrahydrofuran was hydrogenated on 100 mg of 10% palladium-carbon under hydrogen gas atmospheric pressure while stirring overnight. The catalyst was filtered off, and the solvent was removed from the filtrate by evaporation to afford 700 mg of ethyl 3-[2,3-dihydro-3-[3-(2-methoxyphenyl)propanoylamino]-2-oxo-1-phenyl-1H-indol-3-yl]propionate as an amorphous solid.

Example 85

A mixture of 3.89 g of methyl 3-[3-(3,4-dichlorobenzoylamino)-2,3-dihydro-2-oxo-1-pentyl-1H-indol-3-yl]propionate, 16 ml of a 2N sodium hydroxide aqueous solution and 100 ml of methanol was refluxed for 40 minutes. After the reaction mixture was cooled to room temperature, the solvent was removed by evaporation under reduced pressure. The residue was diluted with water, adjusted to pH 4 with 10% hydrochloric acid and then extracted with chloroform. After the extract was washed with water and dried, the solvent was removed by evaporation. The resulting crude crystals were recrystallized from ethyl acetate-hexane to afford 3.34 g of 3-[3-(3,4-dichlorobenzoylamino)-2,3-dihydro-2-oxo-1-pentyl-1H-indol-3-yl]propionic acid as colorless crystals. Melting point: 202° to 204° C., IR (Nujol) (cm$^{-1}$): 3260, 1730, 1675, 1660, FAB-MS (m/z): 463 (MH$^+$), 173 (base).

Example 86

1.5 ml of 4N sodium hydroxide and 5 ml of water were added to a mixed solution of 1.20 g of ethyl 3-[3-(3,4-dichlorobenzoylamino)-2,3-dihydro-2-oxo-1-(3-phenylpropyl)-1H-indol-3-yl]propionate, 20 ml of ethanol and 5 ml of tetrahydrofuran. The mixture was stirred at room temperature for 7 hours. The reaction mixture was concentrated under reduced pressure, diluted with water, then made acidic with 10% hydrochloric acid and extracted with ethyl acetate. After the extract was dried, the solvent was removed by evaporation. The residue was recrystallized from ethanol-ethyl acetate to afford 1.09 g of 3-[3-(3,4-dichlorobenzoylamino)-2,3-dihydro-2-oxo-1-(3-phenylpropyl)-1H-indol-3-yl]propionic acid as colorless needles. Melting point: 242° to 243° C., IR (Nujol) (cm$^{-1}$): 3285, 1715, 1690, 1675, 1615, FAB-MS (m/z): 513 & 511 (MH$^+$).

Example 87

3.79 ml of 1N sodium hydroxide was added to 30 ml of an ethanol solution of 1.70 g of ethyl 3-[3-(2-formyl-1,2,3,4-tetrahydro-3-isoquinolinyl)carbonylamino-2,3-dihydro-2-oxo-1-pentyl-1H-indol-3-yl]propionate. The mixture was stirred at room temperature for 4 hours. After removal of solvent, the residue was dissolved in water, washed with water with diethyl ether, made acidic with 10% hydrochloric acid and then extracted with ethyl acetate. The ethyl acetate layer was further extracted with a sodium hydrogen carbonate aqueous solution. The extract was adsorbed by a non-ionic adsorption resin (trade name: HP-20, produced by Mitsubishi Kasei Corporation) and eluted with water and a water-methanol (1:1) mixed solution. The eluate was lyophilized to afford 1.24 g of sodium 3-[3-(2-formyl-1,2,3,4-tetrahydro-3-isoquinolinyl)carbonylamino-2,3-dihydro-2-oxo-1-pentyl-1H-indol-3-yl]propionate as a pale yellow powder. IR (Nujol) (cm$^{-1}$): 3680 to 2400 (br) , 1710, 1660, 1610, FAB-MS (m/z): 522 (MNa$^+$), 500 (MH$^+$, base).

Examples 88 to 162

By treating the corresponding starting compound in the same manner as described in either of Examples 85 to 87, the compounds in Table 12 to Table 22 were obtained.

TABLE 12

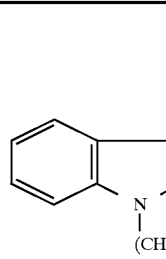

| Example No. | -Y-R$^2$ | Physical constant, etc. |
|---|---|---|
| 88 | 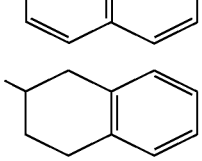 | M.P.: 170–173° C. |
| 89 | | M.P.: 182–190° C. |

TABLE 12-continued

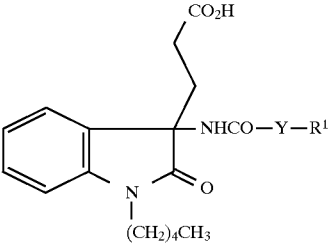

| Example No. | -Y-R² | Physical constant, etc. |
|---|---|---|
| 90 | 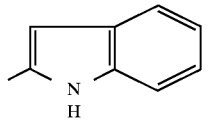 | M.P.: 244–246° C. |
| 91 | 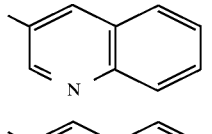 | Caramel |
| 92 | 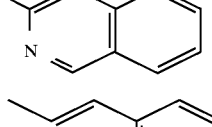 | (Sodium salt) Amorphous |
| 93 | 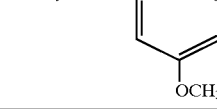 | M.P.: 136–137° C. |
| 94 | 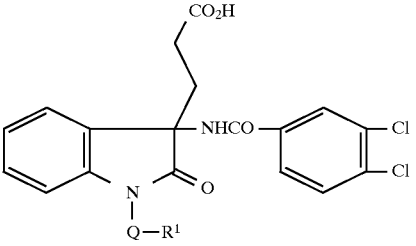 | M.P.: 164–166° C. |

TABLE 13

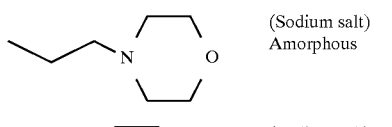

| Example No. | -Q-R¹ | Physical constant, etc. |
|---|---|---|
| 95 | 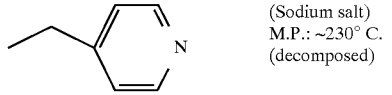 | M.P.: 195–196° C. |
| 96 | 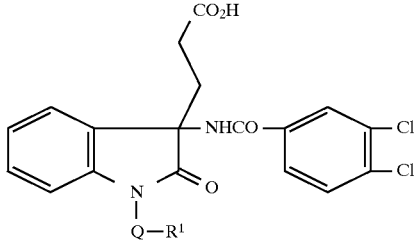 | (Sodium salt) Amorphous |
| 97 | 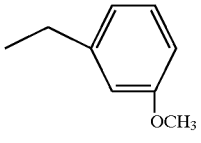 | (Sodium salt) M.P.: ~230° C. (decomposed) |

TABLE 13-continued

| Example No. | -Q-R¹ | Physical constant, etc. |
|---|---|---|
| 98 | $-(CH_2)_3CN$ | M.P.: 108–176° C. (gradually fused) |
| 99 | $-(CH_2)_3OCH_3$ | M.P.: 129–176° C. (gradually fused) |
| 100 | $-(CH_2)_2SCH_3$ | M.P.: 215–216° C. |
| 101 | $-CH_2CO_2C(CH_3)_3$ | M.P.: 194–194.5° C. |

TABLE 14

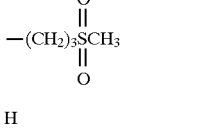

| Example No. | -Q-R¹ | Physical constant, etc. |
|---|---|---|
| 102 | cyclopropylmethyl | M.P.: 133–136° C. |
| 103 | $-(CH_2)_5CH_3$ | M.P.: 204–204.5° C. |
| 104 | $-(CH_2)_4$-phenyl | M.P.: 180–181.5° C. |
| 105 | 3-ethyl-5-methoxyphenyl group | M.P.: 210–211° C. |
| 106 | $-(CH_2)_3SCH_3$ | M.P.: 158.5–160° C. |
| 107 | $-(CH_2)_3S(O)CH_3$ | M.P.: 147–149° C. |
| 108 | $-(CH_2)_3S(O)_2CH_3$ | M.P.: 161.5–163.5° C. |
| 109 | H | M.P.: 269–270° C. |

TABLE 15
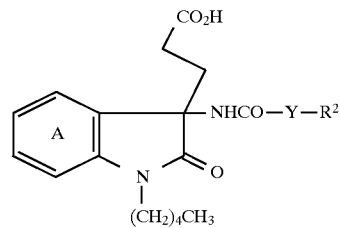
| Example No. | Ring A | —Y—R² | Physical constant, etc. |
|---|---|---|---|
| 110 | (benzene) | CH₂-NH-CH(CH₃)-CH₂-(phenyl) | (Sodium salt) Amorphous |
| 111 | (benzene) | -CH=CH-CH₂-(3-hydroxyphenyl) | M.P.: 215–216° C. |
| 112 | CH₃O-(benzene) | (naphthyl) | M.P.: 217–219° C. |
| 113 | CH₃O-(benzene) | (isoquinolinyl) | M.P.: 200–202° C. |
| 114 | CH₃O-(benzene) | (indolyl) | M.P.: 231–233° C. |
| 115 | CH₃O-(benzene) | (quinolinyl) | M.P.: 265–267° C. |
| 116 | CH₃O-(benzene) | (quinolinyl) | M.P.: 189–191° C. |

TABLE 16
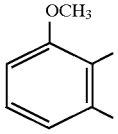
| Example No. | Ring A | Physical constant, etc. |
|---|---|---|
| 117 | 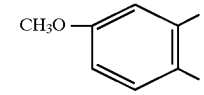 OCH₃ | M.P.: 192.5–194° C. |
| 118 | CH₃O— 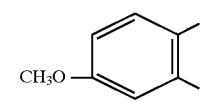 | M.P.: 176–181° C. |
| 119 | CH₃O— 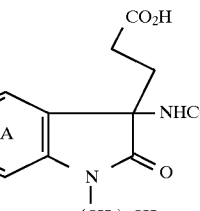 | M.P.: 215–217° C. |
TABLE 16-continued
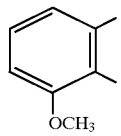
| Example No. | Ring A | Physical constant, etc. |
|---|---|---|
| 120 | 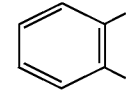 OCH₃ | M.P.: 176–177.5° C. |
TABLE 17
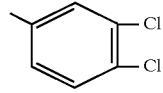
| Example No. | Ring A | —Y—R² | Physical constant, etc. |
|---|---|---|---|
| 121 | 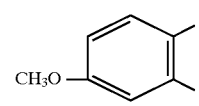 | 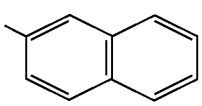 | M.P.: 142–146° C. |
| 122 | CH₃O— 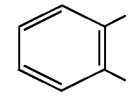 | 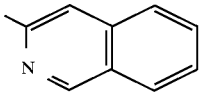 | M.P.: 135–136° C. |
| 123 | 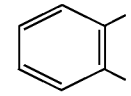 | 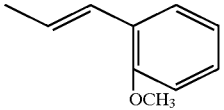 | M.P.: 207–209° C. |
| 124 |  |  OCH₃ | M.P.: 203–206° C. |

TABLE 17-continued

[Structure: indolinone with CO2H-propyl, NHCO-Y-R² at 3-position, N-phenyl substituent, Ring A fused]

| Example No. | Ring A | —Y—R² | Physical constant, etc. |
|---|---|---|---|
| 125 | C₂H₅O-phenyl | naphthyl | M.P.: 125° C. |
| 126 | phenyl | HO-phenyl-CH=CH- | M.P.: 224° C. |
| 127 | phenyl | (2-OCH₃-phenyl)-propyl | M.P.: 185–187° C. |

TABLE 18

[Structure: indolinone with CO2H-propyl, NHCO-Y-R² at 3-position, N-(2-fluorophenyl) substituent, Ring A fused]

| Example No. | Ring A | —Y—R² | Physical constant, etc. |
|---|---|---|---|
| 128 | CH₃O-phenyl | naphthyl | M.P.: 150–157° C. |
| 129 | phenyl | naphthyl | M.P.: 229–229.5° C. |
| 130 | CH₃O-phenyl | isoquinolinyl | (Sodium salt) Amorphous |
| 131 | CH₃O-phenyl | indolyl (NH) | M.P.: 186–188° C. |

TABLE 19

[Structure: indolin-2-one with ring A fused, bearing at 3-position a -CH2CH2CO2H group and -NHCO-Y-R2 group; N-1 substituted with 4-fluorophenyl]

| Example No. | Ring A | —Y—R² | Physical constant, etc. |
|---|---|---|---|
| 132 | CH₃O-(2,3-disubstituted phenyl) | 2-naphthyl | M.P.: 132.5–133° C. |
| 133 | CH₃O-(3,4-disubstituted phenyl) | 2-naphthyl | M.P.: 125–127° C. |
| 134 | CH₃O-(3,4-disubstituted phenyl) | isoquinolin-3-yl | (Sodium salt) Amorphous |
| 135 | CH₃O-(3,4-disubstituted phenyl) | indol-2-yl (NH) | M.P.: 193–195° C. |
| 136 | CH₃O-(3,4-disubstituted phenyl) | lilolidinyl | M.P.: 145–150° C. |
| 137 | CH₃O-(3,4-disubstituted phenyl) | quinolin-3-yl | M.P.: 293–295° C. |
| 138 | CH₃O-(3,4-disubstituted phenyl) | isoquinolin-3-yl | M.P.: 171–173° C. |
| 139 | CH₃O-(3,4-disubstituted phenyl) | 2,3-dihydro-1H-pyrrolizinyl | M.P.: 214–216° C. |

TABLE 20
| Example No. | Ring A | -Q-R¹ | -Y-R² | Physical constant, etc. |
|---|---|---|---|---|
| 140 | 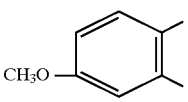 | 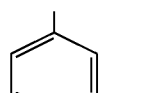 | 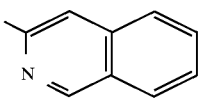 | Amorphous |
| 141 | 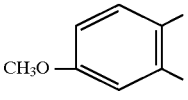 |  | 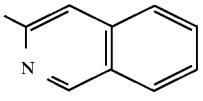 | M.P.: 238–240° C. |
| 142 | 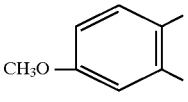 |  | 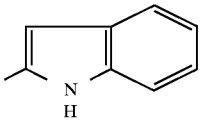 | M.P.: 170–172° C. |
| 143 | 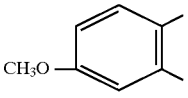 |  | 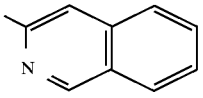 | M.P.: 223–225° C. |
| 144 | 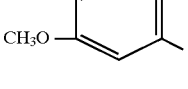 |  | 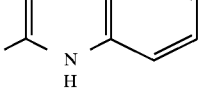 | M.P.: 190–191° C. |
| 145 | 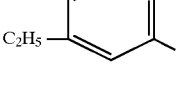 | —(CH$_2$)$_4$CH$_3$ | 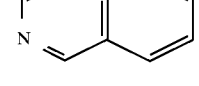 | M.P.: ~125° C. |
| 146 | 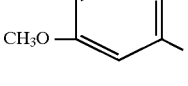 | 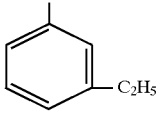 | 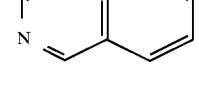 | Amorphous |
| 147 | 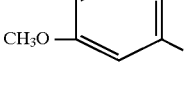 | 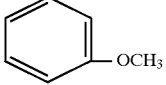 | 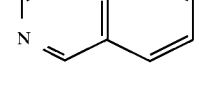 | Amorphous |
| 148 | 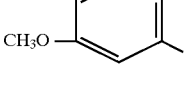 | —(CH$_2$)$_4$CH$_3$ | 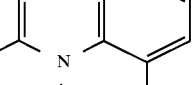 | M.P.: 159–162° C. |

TABLE 21

[Structure: 6-methoxy-1-(4-fluorophenyl)-3-R³-3-(NHCO-Y-R²)-indolin-2-one]

| Example No. | R³ | —Y—R² | Physical constant, etc. |
|---|---|---|---|
| 149 | (CH₂)₂CO₂H | 2-benzothiophenyl | M.P.: 183–186° C. |
| 150 | (CH₂)₂CO₂H | 2-benzimidazolyl | M.P.: 264–266° C. (decomposed) |
| 151 | (CH₂)₂CO₂H | 2-benzofuranyl | Amorphous |
| 152 | (CH₂)₂CO₂H | 5-methylindol-2-yl | M.P.: 250–253° C. |
| 153 | (CH₂)₂CO₂H | 3-methyl-coumarin-4-yl | M.P.: 241–242° C. |
| 154 | CH₂CO₂H | 3-methylisoquinolin-3-yl | M.P.: 212–213° C. |
| 155 | (CH₂)₃CO₂H | 3-methylisoquinolin-3-yl | M.P.: 175–177.5° C. |

TABLE 22

[Structure: indolin-2-one core with ring A fused, CH2CH2CO2H and NHCO-Y-R² substituents at 3-position, N-(4-fluorophenyl) at N1]

| Example No. | Ring A | —Y—R² | Physical constant, etc. |
|---|---|---|---|
| 156 | CH₃O-phenyl | naphthalen-1-yl | M.P.: 243–244° C. |
| 157 | C₂H₅-phenyl | isoquinolin-3-yl | M.P.: 190–192° C. |
| 158 | CH₃O-phenyl | 1H-benzimidazol-2-yl | Amorphous |
| 159 | CH₃O-phenyl | quinoxalin-2-yl | M.P.: 252–253° C. |
| 160 | CH₃O-phenyl | 4,5-dihydropyrrolo-fused | M.P.: 214–216° C. |
| 161 | CH₃O-phenyl | -CH2-naphthalen-2-yl | M.P.: 166–168° C. |
| 162 | CH₃O-phenyl | -CH2-pyridin-2-yl | M.P.: 159–160.5° C. |

Example 163

A mixture of 2.00 g of 3,4-dichloro-N-[3-(2-cyanoethyl)-2,3-dihydro-2-oxo-1-pentyl-1H-indol-3-yl]benzamide, 3.0 g of tributyltin azide ($Bu_3SnN_3$) and 1.5 ml of toluene was stirred at 110° C. for 3 hours. After cooling, a 50 ml of ethanolic 6.4% hydrochloric acid solution was added to the mixture, and the resulting mixture was stirred at room temperature for 30 minutes. After removal of solvent by evaporation, ethyl acetate and then an aqueous saturated potassium fluoride solution were added to the residue, and insolubles were removed by filtration. The ethyl acetate layer was collected by separation, washed with water and evaporated. The residue was dissolved in an aqueous 5% sodium hydroxide solution and washed with water with diethyl ether. After the aqueous layer was made acidic with 10% hydrochloric acid, it was extracted with ethyl acetate. The extract was washed with water and dried, and solvent was evaporated. The residue was recrystallized from ethyl acetate to afford 1.72 g of 3,4-dichloro-N-{2,3-dihydro-2-oxo-1-pentyl-3-[2-(1H-tetrazol-5-yl)ethyl]-1H-indol-3-yl}-benzamide as colorless needles. Melting point: 142° to 147° C., IR (Nujol) ($cm^{-1}$): 3340, 1705, 1655, 1675, 1615, FAB-MS (m/z): 489 & 487 ($MH^+$).

Example 164

0.647 g of N-[3-(2-cyanoethyl)-1-(4-fluorophenyl)-2,3-dihydro-6-methoxy-2-oxo-1H-indol-3-yl]-3- isoquinolinecarboxamide was treated in the same manner as in Example 163 to afford 0.252 g of N-{1-(4-fluorophenyl)-2,3-dihydro-6-methoxy-2-oxo-3-[2-(1H-tetrazol-5-yl)ethyl]-1H-indol-3-yl}-3-isoquinolinecarboxamide. Melting point 154° to 160° C.

Example 165

A mixture of 375 mg of ethyl 3-[2,3-dihydro-3-(1H-indol-2-ylcarbonyl)amino-2-oxo-1-pentyl-1H-indol-3-yl]propionate, 530 mg of acrylonitrile, 3 drops of 1,8-diazabicyclo-[5.4.0]undec-7-ene (DBU) and 4 ml of dimethylformamide was stirred at 80° C. for 22 hours. The reaction mixture was diluted with water and extracted with ethyl acetate. After the extract was washed, dried and then treated with activated charcoal, the solvent was removed by evaporation under reduced pressure to afford a caramel. A mixture of the residue obtained, 1.4 ml of an aqueous 2N sodium hydroxide solution and 10 ml of methanol was stirred at room temperature for 20 hours. After removal of methanol from the reaction mixture by evaporation under reduced pressure, the residue was made acidic with 10% hydrochloric acid and extracted with chloroform. After the extract was dried, the solvent was removed by evaporation under reduced pressure. The residue was recrystallized from diisopropyl ether to afford 150 mg of 3-[3-[1-(2-cyanoethyl)-1H-indol-2-ylcarbonylamino]-2,3-dihydro-2-oxo-1-pentyl-1H-indol-3-yl]propionic acid. Melting point 125° C.

Example 166

(S) -3-amino-1- (4-fluorophenyl) -2,3-dihydro-5-methoxy-3-methyl-2-oxo-1H-indole and 5,6-dihydro-4H-pyrrolo[3,2,1-ij]quinoline-2-carboxylic acid were treated in the same manner as in Example 3-(1) or Example 7-(1) to afford (S)-N-[1-(4-fluorophenyl)-2,3-dihydro-5-methoxy-3-methyl-2-oxo-1H-indol-3-yl]-5,6-dihydro-4H-pyrrolo[3,2,1-ij]quinoline-2-2-carboxamide. Melting point: 223° to 224° C., $[\alpha]_D^{25}$: +58.33° (c=0.240, chloroform).

Examples 167 to 171

By treating the corresponding starting compounds in the same manner as in Example 166, the following compounds were obtained.

Example 167: (S)-N-[1-(2-fluorophenyl)-2,3-dihydro-3-methyl-2-oxo-1H-indol-3-yl]-5,6-dihydro-4H-pyrrolo[3,2,1-ij]quinoline-2-carboxamide. Melting point: 194° to 195° C., $[\alpha]_D^{25}$: +127.8° (c=0.374, chloroform).

Example 168: (S)-N-[1-(4-fluorophenyl)-2,3-dihydro-5-methoxy-3-methyl-2-oxo-1H-indol-3-yl]-1H-indole-2-carboxamide. Melting point: 287° to 288° C., $[\alpha]_D^{25}$: +90.95° (c=0.376, chloroform).

Example 169: (S)-N-[1-(4-fluorophenyl)-2,3-dihydro-5-methoxy-3-methyl-2-oxo-1H-indol-3-yl]-4,5-dihydropyrrolo-[3,2,1-hi]indole-2-carboxamide. Melting point: 277° to 278° C., $[\alpha]_D^{25}$: +42.30° (c=0.312, chloroform).

Example 170: (+)-N-[3-(2-cyanoethyl)-1-(4-fluorophenyl)-2,3-dihydro-6-methoxy-2-oxo-1H-indol-3-yl]-3-isoquinolinecarboxamide. $[\alpha]_D^{25}$: +80.53° (c=0.226, chloroform).

Example 171: (-)-N-[3-(2-cyanoethyl)-1-(4-fluorophenyl)-2,3-dihydro-6-methoxy-2-oxo-1H-indol-3-yl]-3-isoquinolinecarboxamide. $[\alpha]_D^{25}$: -80.70° (c=0.228, chloroform).

Example 172

Under ice cooling, a hydrochloric acid gas was passed through 20 ml of a methanol solution of 1.88 g of (+)-N-[3-(2-cyanoethyl)-1-(4-fluorophenyl)-2,3-dihydro-6-methoxy-2- oxo-1H-indol-3-yl]-3-isoquinolinecarboxamide until the gas was saturated. The mixture was stirred at room temperature for 30 minutes. 140 μl of water was added to the reaction mixture, and the resulting mixture was allowed to stand for 7 days. The reaction mixture was concentrated, and treated with an aqueous sodium hydrogen carbonate solution. Then, ethyl acetate were added to the resulting residue, and the residue was extracted. The organic layer was collected by separation, dried, then filtered and concentrated. The residue was purified by silica gel column chromatography [hexane-ethyl acetate (1:1)] to afford 1.84 g of (+)-methyl 3-{1-(4-fluorophenyl)-2,3-dihydro-3-[(3-isoquinolinyl)carbonylamino]-6-methoxy-2-oxo-1H-indol-3-yl}propionate as a colorless amorphous solid. $[\alpha]_D^{25}$: +53.41° (c=0.468, chloroform).

Example 173

(-)-N-[3-(2-cyanoethyl)-1-(4-fluorophenyl)-2,3-dihydro-6-methoxy-2-oxo-1H-indol-3-yl]-3-isoquinolinecarboxamide was treated in the same manner as in Example 172 to afford (-)-methyl 3-{1-(4-fluorophenyl)-2,3-dihydro-3-[(3-isoquinolinyl)carbonylamino]-6-methoxy-2-oxo-1H-indol-3-yl]-propionate. $[\alpha]_D^{25}$: -53.81° (c=0.446, chloroform).

Example 174

A mixture of 4.21 ml of 1N sodium hydroxide, 1.80 g of (+)-methyl 3-{1-(4-fluorophenyl)-2,3-dihydro-3-[(3-isoquinolinyl)carbonylamino]-6-methoxy-2-oxo-1H-indol-3-yl}propionate, and ethanol (20 ml) was stirred at room temperature overnight. After removal of solvent, the residue was purified by a nonionic adsorption resin (trade name: HP-20, produced by Mitsubishi Kasei Corporation) to afford 1.64 g of (+)-sodium 3-{1-(4-fluorophenyl)-2,3-dihydro-3-[(3-isoquinolinyl)carbonylamino]-6-methoxy-2-oxo-1H-indol-3-yl}propionate as a colorless powder. $[\alpha]_D^{25}$: +72.94° (c=0.414, methanol).

Example 175

(-)-Methyl 3-{1-(4-fluorophenyl)-2,3-dihydro-3-[(3-isoquinolinyl)carbonylamino]-6-methoxy-2-oxo-1H-indol-3-yl}-propionate was treated in the same manner as in Example 174 to afford (-)-sodium 3-{1-(4-fluorophenyl)-2,3-dihydro-3-[(3-isoquinolinyl)carbonylamino]-6-methoxy-2-oxo-1H-indol-3-yl}propionate. $[\alpha]_D^{25}$: -72.41° (c=0.406, methanol).

Example 176

(1) Under argon gas atmosphere, 29.90 ml of acrylonitrile and 62.70 g of potassium carbonate were added to 210 ml of a dimethyl sulfoxide solution of 70.00 g of 3-amino-1-(2-fluorophenyl)-2,3-dihydro-6-methoxy-1H-indol-2-one hydrochloride, and the whole was stirred at room temperature overnight. The reaction mixture was poured into water, and extracted with ethyl acetate. The ethyl acetate extract was washed with water successively with water and a saturated sodium chloride solution, and dried over anhydrous sodium sulfate and then filtered. The filtrate was evaporated to afford 70.70 g of 3-[3-amino-1-(2-fluorophenyl)-2,3-dihydro-6-methoxy-2-oxo-1H-indol-3-yl]propanenitrile as a brown oil.

(2) 70.70 g of the crude product of 3-[3-amino-1-(2-fluorophenyl)-2,3-dihydro-6-methoxy-2-oxo-1H-indol-3-yl]propanenitrile was dissolved in 250 ml of ethyl acetate.

To this solution was added dropwise a solution of 51.21 g of (+)-dibenzoyltartaric acid monohydrate in 150 ml of ethyl acetate under ice cooling. The resulting crystals were collected by filtration and washed with water with ethyl acetate to afford 3-[3-amino-1-(2-fluorophenyl)-2,3-dihydro-6-methoxy-2-oxo-1H-indol-3-yl]propanenitrile (+)-dibenzoyltartrate (41.13 g) as pale yellow crystals, which was dissolved in 180 ml of hot methanol, concentrated, and triturated with ethyl acetate to afford 34.02 g of the above salt as colorless crystals (yield: 22%). $[\alpha]_D^{25}$: +50.0° (c=0.420, methanol). Melting point 155° to 157° C.

(3) Under stirring, 34.02 g of 3-[3-amino-1-(2-fluorophenyl)-2,3-dihydro-6-methoxy-2-oxo-1H-indol-3-yl]propanenitrile (+)-dibenzoyltartrate was partitioned, in a mixed solvent of an aqueous potassium carbonate solution and ethyl acetate. The ethyl acetate layer was collected by separation, washed with water successively with water and a saturated sodium chloride solution and then dried over anhydrous sodium sulfate. After filtration, the filtrate was concentrated under reduced pressure to afford 15.44 g of a colorless oil. The above product was dissolved in 100 ml of anhydrous dimethylformamide, and 10.19 g of sodium 3-isoquinolinecarboxylate, 6.41 g of 1-hydroxybenzotriazole and 10.92 g of N-ethyl-N'-diethylaminopropylcarbodiimide hydrochloride were added to the solution under ice cooling. The whole mixture was stirred at room temperature overnight. The reaction mixture was poured into water, and the mixture was extracted with ethyl acetate. The organic layer was washed with water successively with diluted hydrochloric acid, water, a saturated sodium hydrogen carbonate aqueous solution, water and a saturated sodium chloride solution and dried over anhydrous sodium sulfate. After filtration, the filtrate was concentrated under reduced pressure to afford 23.85 g of (+)-N-[3-(2-cyanoethyl)-1-(2-fluorophenyl)-2,3-dihydro-6-methoxy-2-oxo-1H-indol-3-yl]-3-isoquinolinecarboxamide as a pale yellow oil.

Example 177

In 80 ml of anhydrous methanol was dissolved 23.85 g of the (+)-N-[3-(2-cyanoethyl)-1-(2-fluorophenyl)-2,3-dihydro-6-methoxy-2-oxo-1H-indol-3-yl]-3-isoquinolinecarboxamide crude product, and under ice cooling, a hydrochloric acid gas was passed through the solution until the gas was saturated. Thereafter, 1.71 ml of water was added to the solution. The reaction mixture was refluxed for 1 hour, cooled and then concentrated under reduced pressure. The residue was neutralized with an aqueous saturated sodium hydrogen carbonate solution and then extracted with ethyl acetate. The organic layer was separated, washed with water with a saturated sodium chloride solution and dried over anhydrous sodium sulfate. After filtration, the filtrate was concentrated under reduced pressure, and the resulting residue was purified by silica gel column chromatography (ethyl acetate:hexane (1:1, volume) as an eluant to afford 22.30 g of (+)-methyl 3-[1-(2-fluorophenyl)-2,3-dihydro-3-(3-isoquinolinyl)carbonylamino-6-methoxy-2-oxo-1H-indol-3-yl]propionate as a pale yellow amorphous solid (yield: 91% (from the product of Example 176 (2))). DI-MS (m/z) 513 (MH⁺), 426, 156, 128 (base). $[\alpha]_D^{25}$: +66.2° (c=0.402, chloroform).

Example 178

A mixture of 62.53 g of (+)-methyl 3-[1-(2-fluorophenyl) -2,3-dihydro-3-(3-isoquinolinyl)carbonylamino-6-methoxy-2-oxo-1H-indol-3-yl]propionate, 56.78 ml of a 3N—NaOH aqueous solution and 576 ml of methanol was stirred at room temperature overnight under ice cooling. The reaction mixture was concentrated under reduced pressure, and the residue was made acidic with an aqueous 15% citric acid solution and extracted with ethyl acetate. The organic layer was collected by separation and washed with water successively with water and a saturated sodium chloride solution, and treated with 15 g of activated charcoal was added to the organic layer, and the mixture was dried over anhydrous sodium sulfate. After insolubles were removed by filtration, the filtrate was concentrated under reduced pressure to afford (+)-3-[1-(2-fluorophenyl)-2,3-dihydro-3-(3-isoquinolinyl)carbonylamino-6-methoxy-2-oxo-1H-indol-3-yl]propionic acid as an oily product. $[\alpha]_D^{25}$: +80.3° (c=0.426, chloroform). To the product obtained above were added 7.36 g of sodium carbonate and 200 ml of water. After the solution was concentrated to dryness under reduced pressure, the residue was dissolved in 500 ml of acetonitrile under heating, and the insolubles were filtered off. After cooling, the crystals precipitated from the filtrate were collected by filtration to afford 60.07 g of (+)-sodium 3-[1-(2-fluorophenyl)-2,3-dihydro-3-(3-isoquinolinyl) carbonylamino-6-methoxy-2-oxo-1H-indol-3-yl]propionate as a colorless solid (yield: 95%). Melting point: 206° to 211° C. FAB-MS (m/z): 522 (MH⁺), 177, 23 (base). $[\alpha]_D^{25}$: +89.7° (c=0.406, methanol).

Example 179

1.74 g of potassium carbonate, 5 ml of water and 20 ml of acetonitrile were added to 11.47 g of (+)-3-[1-(2-fluorophenyl)-2,3-dihydro-3-(3-isoquinolinyl) carbonylamino-6-methoxy-2-oxo-1H-indol-3-yl]propionic acid. After removal of solvent under reduced pressure, the residue was dissolved in 100 ml of acetonitrile was added to the residue under heating, and insolubles were filtered off. The filtrate was concentrated, and the residue was dissolved in 100 ml of acetonitrile under heating. After cooling, precipitated crystals were collected by filtration to afford 10.91 g of (+)-potassium 3-[1-(2-fluorophenyl)-2,3-dihydro-3-(3-isoquinolinyl)carbonylamino-6-methoxy-2-oxo-1H-indol-3-yl]-propionate as a colorless solid. Melting point 275° to 277° C. (decomposed). FAB-MS (m/z): 576 (MK⁺), 538 (MH⁺), 192, 39 (base). $[\alpha]_D^{25}$: +91.8° (c=0.438, methanol).

Example 180

(1) A mixture of 60 g of 3-amino-1-(4-fluorophenyl)-2, 3-dihydro-5-methoxy-1H-indol-2-one hydrochloride, 43 g of potassium carbonate, 20 ml of acrylonitrile and 200 ml of dimethyl sulfoxide was stirred at room temperature under argon atmosphere for 2 hours. 2 ml of acrylonitrile was added to the mixture, and stirring was continued overnight. The reaction mixture was poured into ice water and extracted with ethyl acetate. The extract was washed with a saturated sodium chloride solution, dried over anhydrous magnesium sulfate and filtered, the filtrate was concentrated under reduced pressure. Precipitated crystals were collected by filtration to afford 46.8 g of 3-[3-amino-1-(4-fluorophenyl)-2,3-dihydro-5-methoxy-2-oxo-1H-indol-3-yl]propanenitrile. Melting point 136° to 138° C. EI-MS (m/z): 325 (M⁺).

(2) 43.7 g of 3-[3-amino-1-(4-fluorophenyl)-2,3-dihydro-5-methoxy-2-oxo-1H-indol-3-yl]propanenitrile and 40 g of (−)-dibenzoyltartaric acid were dissolved in 300 ml of ethyl acetate, and the solution was allowed to stand at room temperature overnight while stirring gently. Precipitated crystals were collected by filtration and recrystallized from ethyl acetate to afford 26.4 g of 3-[3-amino-1-(4-fluorophenyl)-2,3-dihydro-5-methoxy-2-oxo-1H-indol-3-yl]-propanenitrile (−)-dibenzoyltartrate. Melting point: 157° to 158.5° C. $[\alpha]_D^{20}$: +64.91° (c=0.228, methanol). EI-MS (m/z): 325 (M$^+$). IR (Nujol) (cm$^{-1}$): 1380, 1460, 1690, 1740, 2250.

(3) Ethyl acetate and a saturated sodium hydrogen carbonate aqueous solution were added to 125.1 g of 3-[3-amino-1-(4-fluorophenyl)-2,3-dihydro-5-methoxy-2-oxo-1H-indol-3-yl]propanenitrile (−)-dibenzoyltartrate, and the ethyl acetate layer was collected by separation. The ethyl acetate layer was washed with water with a saturated sodium chloride solution, dried over anhydrous magnesium sulfate and dried, and then evaporated under reduced pressure. The residue was dissolved in 800 ml of dimethylformamide, and to this solution was added 40 g of sodium isoquinoline-3-carboxylate. Further, under ice cooling, 27.4 g of 1-hydroxybenzotriazole and 39 g of N-ethyl-N'-diethylaminopropylcarbodiimide hydrochloride were added to the mixture, and the whole was stirred. The temperature of this solution was gradually returned to room temperature, and the solution was stirred overnight.

The reaction mixture was diluted with water and ethyl acetate, and the ethyl acetate layer was collected by separation. The ethyl acetate extract was washed with water with a saturated sodium chloride solution, dried over anhydrous magnesium sulfate and filtered. The solvent in the resulting solution was removed by evaporation under reduced pressure to afford (+)-N-[3-(2-cyanoethyl)-1-(4-fluorophenyl)-2,3-dihydro-5-methoxy-2-oxo-1H-indol-3-yl]-3-isoquinolinecarboxamide as an oil. $[\alpha]_D^{25}$: +32.52° (c=0.412, methanol).

Example 181

160 g of (+)-N-[3-(2-cyanoethyl)-1-(4-fluorophenyl)-2,3-dihydro-5-methoxy-2-oxo-1H-indol-3-yl]-3-isoquinolinecarboxamide was dissolved in 770 ml of methyl alcohol, and under ice cooling, a hydrochloric acid gas was passed through the solution for about 2 hours. Then, 6.6 ml of water was added, and the whole mixture was refluxed under heating for 1 hour. After returning to room temperature, the reaction mixture was concentrated under reduced pressure and diluted with an aqueous sodium hydrogen carbonate solution and ethyl acetate, and the organic layer was collected by separation. This organic layer was washed with water with a saturated sodium chloride solution, dried over anhydrous magnesium sulfate and filtered, and the solvent was removed by evaporation under reduced pressure. The residue was purified by silica gel column chromatography (ethyl acetate: n-hexane =1:2 to 1:1) to afford (+)-methyl 3-[1-(4-fluorophenyl)-2,3-dihydro-3-(3-isoquinolinyl)carbonylamino-5-methoxy-2-oxo-1H-indol-3-yl]propionate as an amorphous substance. $[\alpha]_D^{25}$: +7.25° (c=0.248, methanol).

Example 182

In 800 ml of methyl alcohol was dissolved 91 g of (+)-methyl 3-[1-(4-fluorophenyl)-2,3-dihydro-3-(3-isoquinolinyl)carbonylamino-5-methoxy-2-oxo-1H-indol-3-yl]propionate. To this solution was added 300 ml of an aqueous 1N sodium hydroxide solution, and the whole mixture was stirred at room temperature for 5 hours. After removal of solvent by evaporation under reduced pressure, the residue was diluted with hydrochloric acid and ethyl acetate, and the organic layer was collected by separation. The organic layer was washed with water with a saturated sodium chloride solution, dried over anhydrous magnesium sulfate and filtered, and the solvent was removed by evaporation under reduced pressure. The residue was crystallized from acetonitrile-diisopropyl ether and collected by filtration to afford 90.59 g of crystals. 10 g of the product collected by filtration was dissolved in a 1.6N potassium hydroxide aqueous solution, and the solution was applied to HP-20 and lyophilized. The resulting amorphous substance was crystallized from ethyl acetate to afford 8.29 g of (+)-potassium 3-[1-(4-fluorophenyl)-2,3-dihydro-3-(3-isoquinolinyl)carbonylamino-5-methoxy-2-oxo-1H-indol-3-yl]propionate (0.3 to 0.6 hydrate). Melting point 280° to 286° C. $[\alpha]_D^{25}$: +13.07° (c=0.260, methanol). FAB-MS (m/z): 576 (MK$^+$), 538 (MH$^+$). IR (Nujol) (cm$^{-1}$): 1520, 1570, 1670, 1730.

Reference Example 1

(1) A solution of 32.3 g (0.149 mole) of 4-methoxy-4'-fluorodiphenylamine in 120 ml of dichloromethane was added dropwise to a stirred solution of 65 ml (0.745 mole) of oxalyl chloride in 65 ml of dichloromethane under ice cooling. The mixture was stirred as such for 1.5 hours. After completion of the reaction and removal of solvent under reduced pressure, 120 ml of dichloromethane was added to the residue, 23.9 g (0.179 mole) of aluminum chloride was added to the mixture under ice cooling, and then the whole was stirred at room temperature overnight. After completion of the reaction, the reaction mixture was treated with 10% hydrochloric acid. The resulting precipitates were collected by filtration, washed with water and then with diethyl ether, and dried to afford 38.7 g of 1-(4-fluorophenyl)-2,3-dihydro-5-methoxy-1H-indol-2,3-dione as red crystals. Melting point 246° to 247° C.

(2) A mixture of 13.55 g (0.05 mole) of the product obtained above, 10.43 g (0.15 mole) of hydroxyamine hydrochloride, 7.95 g (0.075 mole) of sodium carbonate, 500 ml of ethanol and 200 ml of water was refluxed for 1 hour. After completion of the reaction and removal of ethanol under reduced pressure, water was added to the residue, and the resulting precipitates were collected by filtration. The crystals obtained were washed with water and dried to afford 14.3 g of 1-(4-fluorophenyl)-2,3-dihydro-5-methoxy-1H-indole-2,3-dione-3-oxime as yellow crystals. Melting point 217° to 219° C.

(3) A mixture of 14.3 g (0.05 mole) of the product obtained above, 8.2 ml of conc. hydrochloric acid, 3.0 g of 10% palladium-carbon and 500 ml of ethanol was subjected to catalytic reduction reaction at room temperature under hydrogen atmosphere overnight. The catalyst was filtered off, and to the residue obtained by removing the solvent by evaporation under reduced pressure, a mixed solvent of acetone and diethyl ether was added to afford 12.4 g of 3-amino-1-(4-fluorophenyl)-2,3-dihydro-5-methoxy-1H-indol-2-one [=3-amino-1-(4-fluorophenyl)-5-methoxy-1H-indol-2(3H)-one]hydrochloride as colorless crystals. Melting point 170° to 175° C., IR (Nujol) (cm$^{-1}$): 1740, MS (DI, m/z): 272 (M$^+$).

Reference Examples 2 to 7

By treating the corresponding starting compounds in the same manner as in Reference example 1, the following compounds were obtained.

Reference example 2: 3-amino-1-(2-fluorophenyl)-2,3-dihydro-1H-indol-2-one hydrochloride, melting point 182° to 183° C.

Reference example 3: 3-amino-1-phenyl-2,3-dihydro-1H-indol-2-one hydrochloride. Melting point 90° C.

Reference example 4: 3-amino-1-(2-fluorophenyl)-2,3-dihydro-6-methoxy-1H-indol-2-one hydrochloride. Melting point 160° to 161° C. (decomposed).

Reference example 5: 3-amino-2,3-dihydro-6-methoxy-1-phenyl-1H-indol-2-one hydrochloride. Melting point 172° to 175° C. (decomposed).

Reference example 6: 3-amino-1-(4-fluorophenyl)-2,3-dihydro-6-methoxy-1H-indol-2-one hydrochloride. Melting point 180° C. (decomposed).

Reference example 7: 3-amino-1-(3-chlorophenyl)-2,3-dihydro-6-methoxy-1H-indol-2-one hydrochloride. Melting point 168° to 173° C. (decomposed).

Reference Example 8

(1) A stirred solution of 270 mg of sodium hydride was added to 1.00 g of 2,3-dihydro-1H-indol-2,3-dione in dimethylformamide at room temperature. After the reaction mixture was stirred at room temperature for 10 minutes, 5 ml of a dimethylformamide solution of 2.10 g of pentyl bromide was added dropwise thereto. After the reaction mixture was stirred at room temperature for 20 minutes, water was added to the reaction mixture, and the mixture was extracted with ethyl acetate. After the extract was washed with water and dried, the solvent was removed by evaporation. The residue was purified by silica gel column chromatography [ethyl acetate-hexane (1:5)] to afford 1.31 g of 2,3-dihydro-1-pentyl-1H-indol-2,3-dione as orange crystals. Melting point: 50° to 51° C.

(2) 1.23 g of the product obtained above was treated in the same manner as in Reference 1-(2) and (3), to afford 1.31 g of 3-amino-2,3-dihydro-1-pentyl-1H-indol-2-one hydrochloride as colorless crystals (recrystallized from ethanol-diethyl ether). Melting point: 142° to 144° C.

Reference Example 9

14.7 g of 2,3-dihydro-1H-indol-2,3-dione was treated in the same manner as in Reference example 1-(2) and (3), to afford 16.9 g of 3-amino-2,3-dihydro-1H-indol-2-one hydrochloride (recrystallized from ethanol-diethyl ether). Melting point: 199° C.

Reference Example 10

(1) 120 ml of triethylamine and 56.7 ml of acetic anhydride were added dropwise to a stirred solution of 70.5 g of m-anisidine in 500 ml of a methylene chloride under ice cooling. After completion of the dropwise addition, the reaction mixture was washed and dried, and insolubles were filtered off. The filtrate was concentrated, and the residue was recrystallized from hexane-ethyl acetate to afford 80.9 g of N-(3-methoxyphenyl)acetamide as pale yellow needles. Melting point: 81° to 82° C.

(2) 10.65 g of a 60% oil suspension of sodium hydride was suspended in 100 ml of anhydrous dimethylformamide under argon atmosphere. To said suspension were added dropwise under ice cooling 40.00 g of the product obtained above dissolved in 100 ml of dimethylformamide and then 38.23 g of n-pentyl bromide. After elevating the temperature gradually from 0° C. to room temperature, the mixture was stirred for 5 hours. The reaction mixture was poured into water, and a precipitated oil was extracted with ethyl acetate. The extract was washed and dried, and insolubles were filtered off. The filtrate was evaporated to afford 67.76 g of N-(3-methoxyphenyl)-N-pentylacetamide as a pale yellow oil.

(3) 100 ml of conc. hydrochloric acid was added to 200 ml of an ethanol solution of 67.76 g of the product obtained above, and the mixture was refluxed for 24 hours. The reaction mixture was concentrated, and the residue was extracted with chloroform. After the extract was made alkaline with sodium hydrogen carbonate, the organic layer was collected by separation and dried, and insolubles were filtered off. A brown oil obtained by concentrating the filtrate was converted into hydrochloride by ethanol-hydrochloric acid treatment, and then recrystallized from acetone-isopropyl ether to afford 47.05 g of N-pentyl-m-anisidine hydrochloride as colorless needles. Melting point: 110° to 112° C.

(4) 47.00 g of the product obtained above was treated in the same manner as in Reference example 1-(1) to (3), to afford 33.39 g of 3-amino-2,3-dihydro-6-methoxy-1-pentyl-1H-indol-2-one hydrochloride as colorless needles (recrystallized from acetone). Melting point: 178° to 180° C.

Reference Examples 11 to 13

By treating the corresponding starting compounds in the same manner as in Reference example 10, the following compounds were obtained.

Reference example 11: 3-amino-2,3-dihydro-5-methoxy-1-pentyl-1H-indol-2-one hydrochloride. Melting point: 163° to 165° C.

Reference example 12: 3-amino-2,3-dihydro-7-methoxy-1-pentyl-1H-indol-2-one hydrochloride. Melting point: 184.5° to 187° C.

Reference example 13: 3-amino-2,3-dihydro-6-ethyl-1-pentyl-1H-indol-2-one hydrochloride. Melting point: 157° to 159° C.

Reference Example 14

(1) A mixture of 11 g of N-(3-ethylphenyl)acetamide, 9 g of copper powder, 19.8 g of potassium carbonate and 26.7 g of m-bromoanisole was stirred at 200° C. for 3 days. Insolubles were filtered off from the reaction mixture, and the filtrate was purified by silica gel column chromatography [ethyl acetate-hexane (1:3)]. To the resulting substance were added 16.6 g of potassium hydroxide, 8.7 ml of water and 170 ml of ethanol, and the whole was refluxed for 1 hour. The solvent was removed from the reaction mixture by evaporation, and water and ethyl acetate were added to the residue. After the organic layer was collected by separation, washed and dried, the solvent was removed by evaporation to afford 15.08 g of N-(3-ethylphenyl)-N-(3-methoxyphenyl)amine as an oil. IR (Nujol) (cm$^{-1}$): 3400, 1600, 1490, 1460, MS (m/z): 227 (M$^+$, base).

(2) The product obtained above was treated in the same manner as in Reference example 1-(1) to (3), to afford 3-amino-1-(3-ethylphenyl)-2,3-dihydro-6-methoxy-1H-indol-2-one hydrochloride as a foam.

Reference Examples 15 and 16

By treating the corresponding starting compounds in the same manner as in Reference example 14, the following compounds were obtained.

Reference example 15: 3-amino-2,3-dihydro-6-methoxy-1-(3-methoxyphenyl)-1H-indol-2-one hydrochloride. IR (Nujol) (cm$^{-1}$): 1730, 1630, 1600, 1470, 1380, MS (m/z): 284 (M$^+$), 255 (base).

Reference example 16: 3-amino-6-ethyl-1-(4-fluorophenyl)-2,3-dihydro-1H-indol-2-one hydrochloride. Melting point: 213° to 215° C.

Reference Example 17

(1) Under ice cooling, 45 ml of acetic acid was added dropwise over 1 hour to 300 ml of a dichloroethane suspension of 8 g of sodium borohydride. To said mixture were added slowly a solution of 17.48 g of m-anisidine and 16 ml of cyclohexanone in 50 ml of dichloroethane, and the mixture was stirred at room temperature for 40 minutes. The reaction mixture was poured into an aqueous saturated sodium hydrogen carbonate solution and extracted with ethyl acetate. The extract was washed, dried and then purified by silica gel column chromatography [ethyl acetate-hexane (1:5)] to afford 29.37 g of cyclohexyl-(3-methoxyphenyl)-amine as an oil. IR (Neat) (cm$^{-1}$): 3400, 2920, 2850, 1615, 1510, 1500, 1450, MS (m/z): 205 (M$^+$), 162.

(2) The product obtained above was treated in the same manner as in Reference example 1-(1) to (3), to afford 3-amino-1-cyclohexyl-2,3-dihydro-6-methoxy-1H-indol-2-one hydrochloride. Melting point: 185° C.

Reference Example 18

By treating the corresponding starting compound in the same manner as in Reference example 17, 3-amino-1-cyclopentyl-2,3-dihydro-6-methoxy-1H-indol-2-one hydrochloride was obtained. Melting point: 183° to 185° C.

Reference Example 19

(1) Under argon atmosphere and water cooling, 43 ml of a hexane solution of 1.6M n-butyl lithium was added dropwise to a solution of 5.75 g of N-(3-methoxyphenyl)-2,2-dimethyl-propaneamide [synthesized according to R. M. Soll et al., Journal of Organic Chemistry, 53, 2844 (1988)] in 100 ml of tetrahydrofuran. After the mixture was stirred under ice cooling for 2 hours, 18 ml of diethyl oxalate was added to the mixture, and the resulting mixture was stirred at room temperature for additional 2 hours. Water was added to the reaction mixture, and the mixture was extracted with ethyl acetate. After the extract was washed with water and dried, the solvent was removed by evaporation. The residue was purified by silica gel column chromatography [hexane-ethyl acetate (5:1)] and recrystallized from ethyl acetate-hexane to afford 2.86 g of ethyl 2-(2,2-dimethylpropanoylamino)-6-methoxybenzene-α-oxoacetate as lightly yellow crystals. Melting point: 99° to 100° C.

(2) A mixture of 2.85 g of the product obtained above, 30 ml of conc. hydrochloric acid and 30 ml of ethanol was refluxed for 2.5 hours. The solvent was removed from the reaction mixture by evaporation. The residue was diluted with water, made basic with sodium hydrogen carbonate and then extracted with chloroform. After the extract was washed with water and dried, the solvent was removed by evaporation. The residue was digested with chloroform and treated with diisopropyl ether and hexane. Precipitated crystals were collected by filtration to afford 1.49 g of 2,3-dihydro-4-methoxy-1H-indol-2,3-dione as orange crystals. Melting point: 198° to 200° C.

(3) The product obtained above was treated in the same manner as in Reference example 8-(1) to afford 2,3-dihydro-4-methoxy-1-pentyl-1H-indol-2,3-dione. Melting point: 80° to 82° C.

(4) The product obtained above was treated in the same manner as in Reference example 1-(2) and (3) to afford 3-amino-2,3-dihydro-4-methoxy-1-pentyl-1H-indol-2-one hydrochloride. Melting point: 130° to 136° C.

Reference Example 20

(1) In one portion of 4.00 g (0.013 mole) of 3-amino-1-(4-fluorophenyl)-2,3-dihydro-5-methoxy-1H-indol-2-one hydrochloride in 80 ml of anhydrous dichloroethane, 2.69 g (0.0182 mole, 1.4 equivalent) of phthalic anhydride was added to a stirred suspension under argon atmosphere. 2 ml (0.0143 mole) of triethylamine was added dropwise to this mixture over 10 minutes. Then, after the whole was stirred at room temperature for 10 minutes, it was further refluxed over an oil bath overnight. Excessive phthalic anhydride was decomposed by adding a mixture of 2 ml of triethylamine and 2 ml of methanol and refluxing the resulting mixture for 20 minutes. The reaction mixture was concentrated under reduced pressure and then extracted with ethyl acetate. The ethyl acetate layer was washed with water and dried. The residue obtained by removing ethyl acetate by evaporation was recrystallized from hexane-ethyl acetate to afford 4.50 g of 3-(1,2-dihydro-1,3-dioxoisoindol-2-yl)-1-(4-fluorophenyl)-2,3-dihydro-5-methoxy-1H-indol-2-one as colorless crystals. Melting point: 208.5° to 210.0° C., IR (Nujol) (cm$^{-1}$): 1730, 1715, 1495, 1400, 1225, 1210, 750, 715, MS (DI, m/e): 402 (M$^+$, base), 227, 184, 76.

(2) 4.64 g (0.0336 mole) of potassium carbonate and 1.39 ml (0.0224 mole) of methyl iodide were added to a stirred solution of 4.50 g (0.0112 mole) of the product obtained above in 80 ml of acetone under argon atmosphere, and the mixture was vigorously stirred at room temperature overnight. The residue obtained by concentrating the reaction mixture under reduced pressure was extracted with ethyl acetate. The ethyl acetate extract was washed with water and then with a saturated sodium chloride solution and dried over anhydrous sodium sulfate. The residue obtained by removing the solvent by evaporation was recrystallized from ethyl acetate-hexane to afford 3.22 g of 3-(1,2-dihydro-1,3-dioxoisoindol-2-yl)-1-(4-fluorophenyl)-2,3-dihydro-5-methoxy-3-methyl-1H-indol-2-one as pale yellow crystals. Recrystallization from the mother liquor was carried out again to further obtain 0.70 g of the title compound. Melting point: 207° to 208° C., IR (Nujol) (cm$^{-1}$): 1725, 1515, 1490, 1220, 1040, 835, 715, 655, 560, 520, 475, MS (DI, m/z): 416 (M$^+$, base), 401 (M$^+$-Me), 373, 343, 241, 226, 198.

(3) 447 μl (0.00922 mole) of hydrazine hydrate was added dropwise to a stirred solution of 3.20 g (0.00768 mole) of the product obtained above in a mixed solvent of 30 ml of tetrahydrofuran and 30 ml of ethanol at room temperature. After stirring was continued overnight, 20 ml of tetrahydrofuran, 20 ml of ethanol and 447 μl of hydrazine hydrate were added to the mixture, respectively, and the whole was refluxed for 8 hours. After cooling the reaction mixture to room temperature, the resulting precipitates were filtered off, and the filtrate was concentrated to afford a residue. This residue was triturated with ethyl acetate. The resulting precipitates were filtered off and the filtrate was evaporated under reduced pressure, and the residue was purified by silica gel column chromatography [chloroform:ethyl acetate (1:1)] to afford 2.10 g of 3-amino-1-(4-fluorophenyl)-2,3-dihydro-5-methoxy-3-methyl-1H-indol-2-one as colorless needles. Melting point: 163° to 164° C., IR (Nujol) (cm$^{-1}$): 1710, 1610, 1490, 1225, 1200, 1000, 835, 715, 655, 560, 520, 475, FAB-MS (m/z): 287 (MH$^+$) , 286 (M$^+$) , 270 (M$^+$-NH$_2$ base) , 258 (M$^+$-CO).

Reference Example 21

Under argon atmosphere, 1.2 ml of acrylonitrile and 4.48 g of potassium carbonate were added to a stirred suspension of 5.00 g of 3-amino-1-(4-fluorophenyl)-2,3-dihydro-6-methoxy-1H-indol-2-one hydrochloride in dimethyl sulfoxide (30 ml), and the mixture was stirred at room temperature for 9 hours. The reaction mixture was poured into water and extracted with ethyl acetate. After the extract was washed, dried and then filtered, the filtrate was concentrated under reduced pressure. The residue was purified by silica gel column chromatography [chloroform-ethyl acetate (1:1)] to afford 3.48 g of 3-[3-amino-1-(4-fluorophenyl)-2,3-dihydro-6-methoxy-2-oxo-1H-indol-3-yl]propanonitrile as a pale yellow oil.

Reference Example 22

Optical resolution of 3-amino-1-(4-fluorophenyl)-2,3-dihydro-5-methoxy-3-methyl-1H-indol-2-one (1) 9.26 g of dl-3-amino-1-(4-fluorophenyl)-2,3-dihydro-5-methoxy-3-methyl-1H-indol-2-one and 11.72 g of dibenzoyl-L-tartaric acid (hereinafter referred to as DBT) were dissolved with 80 ml of ethyl acetate under heating. After removal of ethyl acetate, 40 ml of ethyl acetate was added again to the residue, and 20 ml of diisopropyl ether was added to the mixture under heating. After cooling, the resulting precipitates were collected by filtration, washed with water with diisopropyl ether-ethyl acetate (1:1 v/v) and dried to afford 7.71 g of a corresponding (−)-DBT salt of a (S) isomer as a colorless powder. Melting point: 164.5° to 167° C. (decomposed). $[\alpha]_D^{25}$: −78.12° (c=0.896, MeOH), optical purity: 99.7% ee (measured by optically active HPLC described below).

Free base: (S)-3-amino-1-(4-fluorophenyl)-2,3-dihydro-5-methoxy-3-methyl-1H-indol-2-one, melting point: 160° to 161° C. $[\alpha]_D^{25}$: −72.38° (c=1.014, CHCl$_3$).

(2) The filtrate was concentrated, and the residue was extracted with ethyl acetate. The extract was treated with an aqueous sodium hydrogen carbonate solution, washed with water and then with an aqueous sodium chloride solution, dried over anhydrous sodium sulfate, and the solvent was removed by evaporation under reduced pressure. To the residue was added 6.45 g of dibenzoyl-D-tartaric acid, and the mixture was dissolved with 20 ml of ethyl acetate under heating. After cooling, precipitated crystals were collected by filtration, washed with water with 30 ml of isopropyl ether-ethyl acetate (1:1 v/v) and dried to afford 8.31 g of a corresponding (+)-DBT salt of a (R) isomer as a colorless powder. Melting point: 163.0° to 164° C. (decomposed). $[\alpha]_D^{25}$: +76.29° (c=0.928, MeOH), optical purity: 99.9% ee (measured by optically active HPLC described below).

Free base: (R)-3-amino-3-methyl-1-(4-fluorophenyl)-5-methoxy-2,3-dihydro-1H-indol-2-one, melting point: 160° to 161° C. $[\alpha]_D^{25}$: +74.05° (c=1.426, CHCl$_3$).

(3) Determination of an absolute configuration was carried out by X-ray structure analysis of a 3-(p-toluenesulfonyl)-amino derivative of the above compound.

Measurement of Optical Purity

Conditions of HPLC

Column: Optipac XC, 3.9×300 mm (produced by Waters Co.)

Eluent: hexane-isopropanol (50/50 v/v)

Flow rate: 0.5 ml/min

Detection wavelength: UV 254 nm

Under the above conditions, the dl isomer was separated. Retention time (R) isomer: 9.27 min (S) isomer: 15.80 min.

Reference example 23 dl-3-amino-1-(2-fluorophenyl)-2,3-dihydro-3-methyl-1H-indol-2-one was treated in the same manner as in Reference example 22, to afford the following compounds.

(−)-DBT salt of (R) isomer: melting point 167.5° to 169.5° C. $[\alpha]_D^{20}$: −60.14° (c=0.562, MeOH), 99.3% ee.

Free base: (R)-3-amino-1-(2-fluorophenyl)-2,3-dihydro-3-methyl-1H-indol-2-one, $[\alpha]_D^{20}$: +63.33° (c=0.960, CHCl$_3$).

(+)-DBT salt of (S) isomer: melting point 165.5° to 167° C., $[\alpha]_D^{20}$: +59.51° (c=0.578, MeOH), 99.2% ee.

Free base: (S)-3-amino-3-methyl-1-(2-fluorophenyl)-2,3-dihydro-1H-indol-2-one, $[\alpha]_D^{20}$: −63.46° (c=0.936, CHCl$_3$).

Reference example 24 dl-3-[3-amino-1-(4-fluorophenyl)-2,3-dihydro-6-methoxy-2-oxo-1H-indol-3-yl]propanonitrile was treated in the same manner as in Reference example 22, to afford the following compounds.

(−)-DBT salt: melting point 175° to 177° C., $[\alpha]_D^{25}$: −67.94° (c=0.836, MeOH), 99.9% ee.

(+)-DBT salt: melting point 169° to 170° C., $[\alpha]_D^{25}$: +62.14° C. (c=0.856, MeOH), 99.9% ee.

Utilizability in Industry

The compound of the present invention and a salt thereof have excellent antagonistic actions on cholecystokinin and exhibit excellent actions of inhibiting secretion of pancreatic juice so that they are useful as a prophylactic or treating agent of diseases of a digestive system such as pancreatic disorder and gastrointestinal diseases, etc. As the pancreatic disorder, there may be mentioned acute pancreatitis, chronic pancreatitis or pancreatic cancer, etc. As the gastrointestinal diseases, there may be mentioned irritable bowel syndrome, regurgitant esophagitis, non ulcer dyspepsia, etc. Further, as other diseases of a digestive system, there may be mentioned biliary colics, etc. Further, the compound of the present invention has low toxicity so that it can be a medicine having high safety when it is used as a medicine.

We claim:

1. A 2-oxoindoline derivative represented by the formula (I):

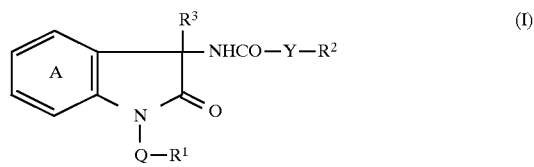

wherein Ring A represents a benzene ring which is substituted in the 5-position or 6-position by a lower alkyl group or a lower alkoxy group, R$^1$ represents a phenyl group which is substituted by a halogen atom, a lower alkyl group or a lower alkoxy group, R$^2$ represents a naphthyl group, indolyl group, isoquinolyl group, benzimidazolyl group or a group represented by the formula:

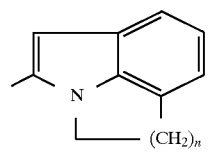

wherein n represents 1 or 2,

R$^3$ represents a lower alkyl group which is substituted by a carboxyl group, a cyano group or a tetrazolyl group, Q represents a single bonding arm, and Y represents a single bonding arm, or a pharmaceutically acceptable salt thereof.

2. The compound according to claim 1, wherein Ring A is a benzene ring which is substituted in the 5-position or 6-position by a lower alkyl group or a lower alkoxy group, $R^1$ is a phenyl group which is substituted by a halogen atom, a lower alkyl group or a lower alkoxy group, $R^2$ is naphthyl group, indolyl group, isoquinolyl group, benzimidazolyl group or a group represented by the formula:

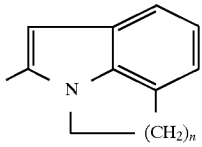

$R^3$ is a lower alkyl group which is substituted by a carboxyl group or a tetrazolyl group, Q is a single bonding arm, and Y is a single bonding arm.

3. The compound according to claim 2, wherein Ring A is a benzene ring which is substituted in the 6-position by a lower alkyl group or a lower alkoxy group, $R^1$ is a halogenophenyl group, $R^2$ is isoquinolyl group, and $R^3$ is a carboxyl-lower alkyl group.

4. A process for preparing a 2-oxoindoline derivative represented by the formula (I):

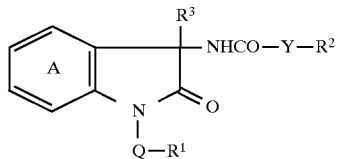

wherein Ring A represents a benzene ring which is substituted in the 5-position or 6-position by a lower alkyl group or a lower alkoxy group, $R^1$ represents a phenyl group which is substituted by a halogen atom, a lower alkyl group or a lower alkoxy group, $R^2$ represents a naphthyl group, indolyl group, isoquinolyl group, benzimidazolyl group or a group represented by the formula:

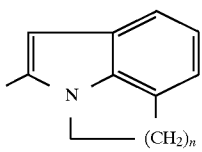

wherein n represents 1 or 2,
$R^3$ represents a lower alkyl group which is substituted by a carboxyl group, a cyano group or a tetrazolyl group, Q represents a single bonding arm, and Y represents a single bonding arm, or a pharmaceutically acceptable salt thereof, which comprises reacting an amine compound represented by the formula (II):

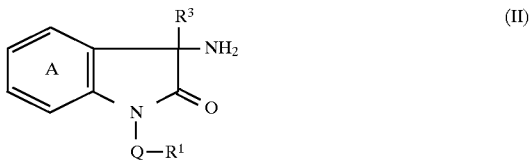

or a salt thereof with a carboxylic acid compound represented by the formula (III):

wherein $R^2$ and Y have the same meanings as described above, an acid halide thereof or a salt thereof, and, if desired, converting the resulting compound into a pharmaceutically acceptable salt thereof.

5. A medical composition which comprises an effective amount for treatment of at least one compound according to claim 1 and a pharmaceutically acceptable carrier or diluent.

6. A method for treating diseases of pancreatic disorder in which cholecystokinin is involved, which comprises administering an effective amount for treatment of at least one compound according to claim 1 to a patient.

7. 3-{1-(2-Fluorophenyl)-2,3-dihydro-3-(3-isoquinolyl)-carbonylamino-6-methoxy-2-oxo-1H-indol-3-yl} propionic acid or a pharmaceutically acceptable salt thereof.

8. Sodium 3-{1-(2-fluorophenyl)-2,3-dihydro-3-(3-isoquinolyl)carbonylamino-6-methoxy-2-oxo-1H-indol-3-yl}-propionate.

9. Sodium (+)-3-{1-(2-fluorophenyl)-2,3-dihydro-3-(3-isoquinolyl)carbonylamino-6-methoxy-2-oxo-1H-indol-3-yl}-propionate.

10. A method for treating diseases of acute pancreatitis and chronic pancreatitis in which cholecystokinin is involved, which comprises administering an effective amount for treatment of at least one compound according to claim 1.

11. A method for treating diseases of acute pancreatitis in which cholecystokinin is involved, which comprises administering an effective amount for treatment of at least one compound according to claim 1.

* * * * *